(12) United States Patent
Yoshikawa et al.

(10) Patent No.: US 10,444,133 B2
(45) Date of Patent: Oct. 15, 2019

(54) MOLECULAR WEIGHT MEASUREMENT METHOD AND MOLECULAR WEIGHT MEASUREMENT APPARATUS

(71) Applicant: NATIONAL INSTITUTE FOR MATERIALS SCIENCE, Ibaraki (JP)

(72) Inventors: Genki Yoshikawa, Ibaraki (JP); Kota Shiba, Ibaraki (JP)

(73) Assignee: NATIONAL INSTITUTE FOR MATERIALS SCIENCE, Ibaraki (JP)

(*) Notice: Subject to any disclaimer, the term of this patent is extended or adjusted under 35 U.S.C. 154(b) by 102 days.

(21) Appl. No.: 15/555,198

(22) PCT Filed: Mar. 4, 2016

(86) PCT No.: PCT/JP2016/056901
§ 371 (c)(1),
(2) Date: Sep. 1, 2017

(87) PCT Pub. No.: WO2016/143719
PCT Pub. Date: Sep. 15, 2016

(65) Prior Publication Data
US 2018/0052085 A1 Feb. 22, 2018

(30) Foreign Application Priority Data
Mar. 6, 2015 (JP) .................. 2015-045316

(51) Int. Cl.
*G01N 9/00* (2006.01)
*G01N 5/02* (2006.01)
(Continued)

(52) U.S. Cl.
CPC ............... *G01N 9/00* (2013.01); *G01N 5/02* (2013.01); *G01N 9/002* (2013.01); *G01N 11/00* (2013.01);
(Continued)

(58) Field of Classification Search
CPC ............ G01N 9/00; G01N 9/002; G01N 5/02; G01N 11/00; G01N 29/36; G01N 29/022; G01N 2291/0427
See application file for complete search history.

(56) References Cited

U.S. PATENT DOCUMENTS

2002/0178787 A1 12/2002 Matsiev et al.
2005/0145019 A1 7/2005 Matsiev et al.
(Continued)

FOREIGN PATENT DOCUMENTS

| JP | 2013-15362 | 1/2013 |
| JP | 2013-015362 | 1/2013 |
| WO | 2005/031300 | 4/2005 |

OTHER PUBLICATIONS

Li et al., Gas Ambient Dependence of Quality Factor in MEMS Resonators, 2009 IEEE Sensors Conference, pp. 1040-1043 (Year: 2009).*

(Continued)

*Primary Examiner* — Toan M Le
(74) *Attorney, Agent, or Firm* — Wenderoth, Lind & Ponack, L.L.P.

(57) ABSTRACT

A sample in a gas state to be measured is forced to impinge on a structure in which a change in a characteristic including a mechanical deformation, an optical change, an electric change and a magnetic change is exerted due to the impingement of a gaseous sample, a gasified liquid sample or solid sample to cause at least one of changes in characteristics including a mechanical deformation, an optical change, an electric change and a magnetic change; and the molecular weight of the sample in a gas state is obtained.

16 Claims, 16 Drawing Sheets

(51) Int. Cl.
*G01N 29/02* (2006.01)
*G01N 29/36* (2006.01)
*G01N 11/00* (2006.01)

(52) U.S. Cl.
CPC ......... *G01N 29/022* (2013.01); *G01N 29/36* (2013.01); *G01N 2291/0427* (2013.01)

(56) References Cited

U.S. PATENT DOCUMENTS

| | | |
|---|---|---|
| 2006/0075803 A1 | 4/2006 | Boisen et al. |
| 2006/0230817 A1 | 10/2006 | Schilowitz et al. |
| 2007/0028668 A1* | 2/2007 | Goto .................. F04B 19/006 73/24.06 |
| 2010/0013456 A1 | 1/2010 | Montelius et al. |
| 2013/0261995 A1 | 10/2013 | Jiang et al. |
| 2014/0305191 A1 | 10/2014 | Schmid et al. |

OTHER PUBLICATIONS

International Search Report dated May 17, 2016 in International Application No. PCT/JP2016/056901.
J. Fritz, et al., "Translating Biomolecular Recognition into Nanomechanics", Science vol. 288, Apr. 14, 2000, pp. 316-318.
M.K. Baller et al., "A cantilever array-based artificial nose", Ultramicroscopy 82, pp. 1-9 (2000).
Faith A. Morrison, "Data Correlation for Drag Coefficient for Sphere", Department of Chemical Engineering, Michigan Technological University, Houghton, MI, pp. 1-2, Nov. 2016.
Extended European Search Report dated Sep. 17, 2018 in European patent application No. 16761689.5.
Communication pursuant to Article 94(3) EPC dated Jun. 25, 2019 in corresponding European Patent Application No. 16761689.5.

* cited by examiner

MOLECULAR WEIGHT MEASUREMENT METHOD AND MOLECULAR WEIGHT MEASUREMENT APPARATUS

TECHNICAL FIELD

The present invention relates to a molecular weight measurement method and a measurement apparatus, by which the molecular weight of a gas state sample is determined on the basis of a mechanical deformation or changes in optical, electric and magnetic properties, which are caused in a structure by a relative motion between the gas state sample and the structure by applying a flow of a gas, or a gasified liquid sample or solid sample to the structure, or conversely, by allowing the structure to move in these gas state samples, or the like.

BACKGROUND ART

To measure a molecular weight of a gas, classical methods such as a method in which an intended gas is collected in a container such as a bag and the mass thereof is measured, and a method utilizing a buoyant force of a gas are known. Since a mass is measured mainly by a balance in these methods, a relatively large amount of gas sample is required, and thus these methods require labor and time for the measurement. Furthermore, there is also a problem that it is difficult to handle the case when the composition of an intended gas changes over time.

Besides such classical methods, a mass analyzer configured to ionize molecules and separate the ionized molecules by an electric or magnetic effect is exemplified. However, in this case, a large-sized and expensive apparatus is required. Therefore, it is not practical in many cases to bring a mass analyzer in a place where an intended gas is present and conduct a measurement.

On the other hand, Patent Literature 1 describes an apparatus for measuring a molecular weight of a gas including: a measurement chamber to be filled with a gas to be measured; a vibrator placed in the measurement chamber; an excitation measurement unit that is configured to excite the vibrator and to measure an excitation parameter of the vibrator; a pressure gauge head that is configured to measure a pressure of the gas in which the vibrator is placed; and a temperature gauge head that is configured to measure a temperature of the vibrator, wherein the apparatus includes a calculation unit that is configured to calculate a molecular weight of the gas from the excitation parameter measured in the excitation measurement unit, the pressure measured in the pressure gauge head, and the temperature measured in the temperature gauge head. It is asserted that a molecular weight can be measured by a downsized apparatus on a real-time basis by this molecular weight measurement apparatus.

However, in the case of the molecular weight measurement apparatus of Patent Literature 1, it is necessary to arrange the vibrator with an oscillator so that an alternating-current voltage is applied from a circuit of a driving/measurement unit outside and the frequency thereof automatically becomes identical with a resonance frequency of the vibrator. Furthermore, in the molecular weight measurement apparatus of Patent Literature 1, an excitation parameter measurement apparatus for measuring an applied electric voltage, a flowing electrical current and a frequency, and an amplitude adjusting apparatus for controlling an applied alternating-current voltage are also necessary, and further improvement in downsizing of the apparatus for the simple measurement of a molecular weight is desired.

SUMMARY OF INVENTION

Technical Problem

The object of the present invention is to provide a molecular weight measurement method and a molecular weight measurement apparatus by which a molecular weight of a gas can be measured in real-time using a small-sized and simple device, on the basis of a principle obtained by combining fluid dynamics, thermodynamics and mechanics, providing a completely different approach compared to the above-mentioned conventional technology.

Solution to Problem

The molecular weight measurement method of the present invention is characterized as follows.

The method comprises the steps of preparing a structure that causes a change in characteristic including a mechanical deformation, an optical change, an electric change, and a magnetic change by letting a gaseous sample or gasified liquid or solid sample on a surface thereof, causing a change in the characteristic of the structure by letting a sample in a gas state to be measured to imping on the structure, the change in a characteristic being at least one selected from the group consisting of a mechanical deformation, an optical change, an electric change, and a magnetic change, and obtaining a molecular weight of the sample in a gas state based on the amount of the change.

The change in property which occurs in the structure is a mechanical deformation, and the method comprises the steps of deforming the structure by letting the sample in a gas state to be measured to impinge on the structure, and obtaining the molecular weight of the gas based on the amount of the deformation of the structure.

A drag force $F_D$ by the sample in a gas state is calculated based on the amount of the deformation of the structure; and the molecular weight M of the gas is obtained based on the following mathematical formula:

[Mathematical Formula 1]

$$F_D = \frac{PV^2 C_D A}{2RT} M.$$

wherein, in the mathematical formula, R is a gas constant, T is a temperature of the gas, P is a pressure of the gas, V is a relative velocity of the gas, $C_D$ is a drag coefficient, and A is a surface area on which the drag force is applied.

The sample in a gas state is provided as a jet flow to the structure.

The structure is a cantilever.

The drag force is provided by the following mathematical formula:

[Mathematical Formula 2]

$$F_D = \frac{9wC_D L M^3 P^3 Q^4}{8\pi^4 \mu^2 l^4 H^2 R^3 \left(\frac{3x^2 M^2 P^2 Q^2}{16\pi^2 \mu^2 l^2 H^2 R^2 T^2} + 1\right)^4 T^3}$$

wherein, in the mathematical formula, $\mu$ is a kinetic viscosity coefficient of a gas that flows out at a flow rate Q from an outlet of a pipe having a diameter of 1 as an axially symmetric jet flow and impinge at a drag coefficient $C_D$ on the structure; the structure is an object having a width w and a length L located at a distance H from the outlet; x is a distance in the vertical direction with respect to a jet flow axis from a center point of the outlet; and α is a number obtained from a relationship between a Reynolds number Re and the drag coefficient $C_D$ obtained by the following mathematical formula:

[Mathematical Formula 3]

$$C_D = \frac{\alpha}{\sqrt{Re}}.$$

The structure is a cantilever.
The Reynolds number Re is provided by the following formula:

[Mathematical Formula 4]

$$Re = \frac{\rho V l}{\mu}.$$

Depending on conditions, the Reynolds number Re is provided by the following formula:

[Mathematical Formula 5]

$$Re = \frac{\rho V w}{\mu}.$$

The amount of the deformation of the cantilever is provided by the following formula:

[Mathematical Formula 6]

$$z(x) = \left[-16\pi^2\alpha\mu^2 l^2 wxH^2[\text{atan}(\beta L) - \text{atan}(\beta x)]R^2 T^2 - 4\sqrt{3}\,\pi\alpha\mu l wxH(x-L)MPQRT - 3\alpha w\{(3x-2L)L^2\text{atan}(\beta L) - x^3\text{atan}(\beta x)\}M^2 P^2 Q^2\right] \Big/ \left[2^{9/2}\pi^2 l^{5/2}E\sqrt{H}\,IMPRT\right]$$

and a free end of the cantilever is placed on the jet flow axis with x=0.

the structure is deformed by moving the structure in a space containing the gaseous sample or a gasified liquid sample or solid sample to be measured.

The amount of the deformation of the structure is measured by a deformation measurement means that is capable of optically detecting deformation of the structure.

The molecular weight measurement apparatus of the present invention is characterized as follows.

The apparatus comprises a chamber having an inlet from which a gaseous sample, or a gasified liquid sample or solid sample is introduced, and having a cantilever therein, a sample feeding means feeding a sample in a gas state from the inlet into the chamber to let the sample in a gas state to impinge on the cantilever, a deformation amount measurement means measuring an amount of deformation of the cantilever associated with impingement of the gaseous sample, or the gasified liquid sample or solid sample, and a calculation means calculating a molecular weight of the sample in a gas state based on the amount of the deformation of the cantilever.

The cantilever has a width w and a length L, and is disposed at a distance H from the outlet of a pipe having a diameter l, and the calculation means is arranged to be capable of calculating a molecular weight M of a gas based on a relational formula between a deformation amount z (x) of the cantilever and the molecular weight M of the gas, provided by the following mathematical formula:

[Mathematical Formula 7]

$$z(x) = \left[-16\pi^2\alpha\mu^2 l^2 wxH^2[\text{atan}(\beta L) - \text{atan}(\beta x)]R^2 T^2 - 4\sqrt{3}\,\pi\alpha\mu l wxH(x-L)MPQRT - 3\alpha w\{(3x-2L)L^2\text{atan}(\beta L) - x^3\text{atan}(\beta x)\}M^2 P^2 Q^2\right] \Big/ \left[2^{9/2}\pi^2 l^{5/2}E\sqrt{H}\,IMPRT\right]$$

wherein $$\beta = \frac{\sqrt{3}\,MPQ}{4\pi\mu l HRT},$$

and a free end of the cantilever is located at the position on the jet flow axis with x=0, and in the mathematical formula, μ is a kinetic viscosity coefficient of a gas that is flowed out at a flow rate Q from an outlet of a pipe having a diameter of 1 as an axially symmetric jet flow and impinges on the structure with a drag coefficient $C_D$; x is a distance in the vertical direction with respect to the jet flow axis from a center point of the outlet; and α is a number obtained from a relationship between a Reynolds number Re and the drag coefficient $C_D$ represented by the following formula:

[Mathematical Formula 8]

$$C_D = \frac{\alpha}{\sqrt{Re}}$$

The Reynolds number Re is provided by the following formula:

[Mathematical Formula 9]

$$Re = \frac{\rho V l}{\mu}.$$

Depending on conditions, the Reynolds number Re is provided by the following formula:

[Mathematical Formula 10]

$$Re = \frac{\rho V w}{\mu}.$$

Advantageous Effects of Invention

According to the molecular weight measurement method of the present invention, it becomes possible to measure the molecular weights of almost all kinds of gases and mixed gases thereof, or of gasified liquid samples and solid samples in real-time by using a simple and small-sized apparatus. Furthermore, since it becomes possible to measure the molecular weight of a gas in real-time, it becomes possible to observe gas components that are generated during a chemical reaction, and thus it becomes possible to evaluate the degree of progress of the chemical reaction. Furthermore, according to the molecular weight measurement device of the present invention, the apparatus can be downsized and thus anybody can easily measure a molecular weight of a gas anytime and anywhere; for example, it will be possible to measure changes in environments, and the like. Furthermore, since the molecular weight measurement apparatus of the present invention utilizes a physical impingement phenomenon of gas molecules, the apparatus can be repeatedly used without applying a special treatment to the structure on which the gas impinges or replacing consumables frequently.

DESCRIPTION OF EMBODIMENTS

Figure 1:
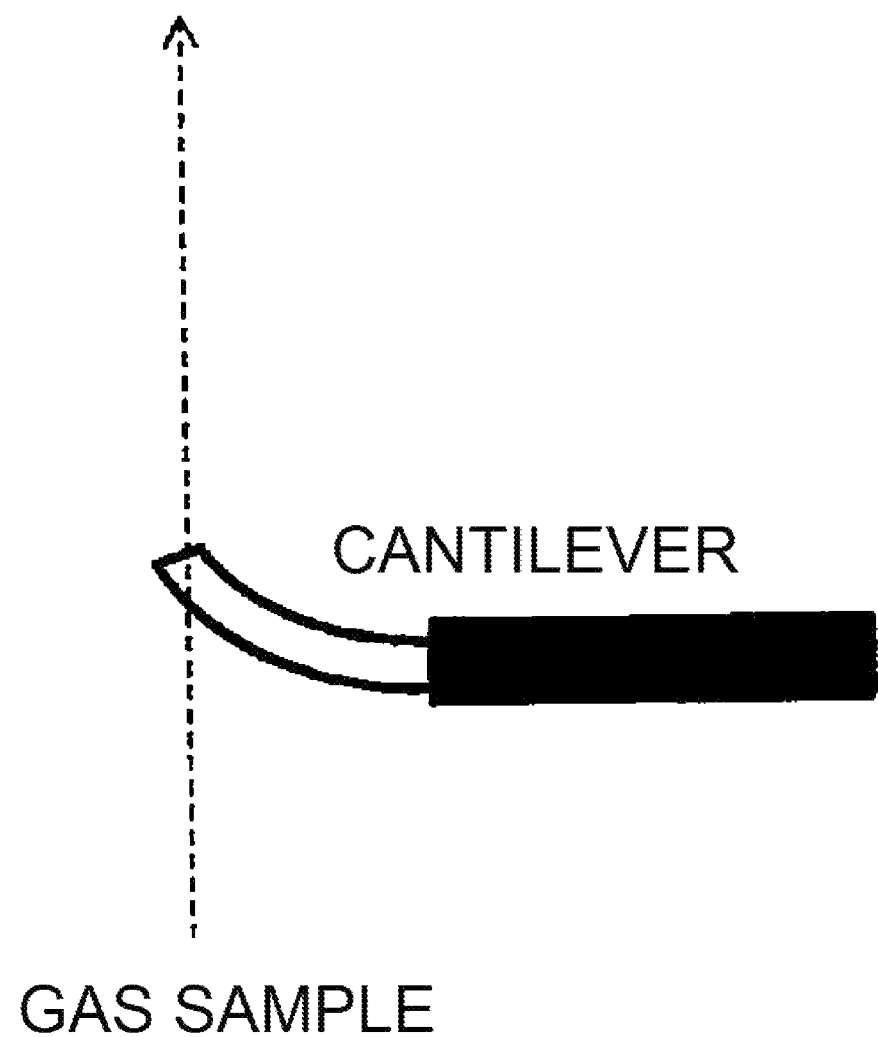
FIG. 1 is a conceptional drawing that explains the principle of the present invention.

The molecular weight measurement method of the present invention obtains a molecular weight of a gas state sample (in the case when the sample is a mixed gas, an average molecular weight thereof) by utilizing a structure that causes a mechanical deformation or changes in optical, electric and magnetic properties by an sample flow.

The molecular weight measurement method of the present invention will be explained below. The symbols used in the present invention are defined as shown in the following Table 1.

TABLE 1

| | | |
|---|---|---|
| Drag coefficient | $C_D$ | — |
| Drag force | $F_D$ | N |
| Surface area on which drag force applied | A | $m^2$ |
| Density of gas | ρ | $kg\ m^{-3}$ |
| Relative velocity of gas | V | $ms^{-1}$ |
| Reynolds number | Re | — |
| Dynamic viscosity | μ | $Nsm^{-2}$ |
| Diameter of pipe | l | m |
| Pressure of gas | P | $Nm^{-2}$ |
| Molecular weight | M | $kg\ mol^{-1}$ |
| Gas constant | R | $J\ mol^{-1}\ K^{-1}$ |
| Temperature of gas | T | K |
| Distance measured along the jet axis from the origin of the jet | H | m |
| Distance measured perpendicular to the jet axis from the origin of the jet | x | m |
| Axial momentum flux across any plane normal to the axis of the jet | J | $kg\ ms^{-1}$ |
| Young's modulus of cantilever | E | $Nm^{-2}$ |
| Second moment of area of cantilever | I | $m^4$ |
| Deformation amount of cantilever | z | m |
| Length of cantilever | L | m |
| Width of cantilever | w | m |
| Thickness of cantilever | t | m |
| Flow rate | Q | $m^3s$ |

In an exemplary embodiment of the molecular weight measurement method of the present invention, mechanical deformation occurs in the structure due to the impingement of a gas sample, or a gasified liquid sample or solid sample. A gas state sample to be measured is allowed to impinge on or collide with this structure to deform the structure, and a drag $F_D$ is calculated from a deformation amount of this structure, and a molecular weight M of the gas is obtained.

The mathematical formula for obtaining the molecular weight M in the molecular weight measurement method of the present invention is derived as follows.

A general mathematical formula that provides the drag force $F_D$, which is a force generated when a gas having a density ρ impinge on an object having a surface area A at a velocity V by a drag coefficient $C_D$ is provided by the following mathematical formula (1):

[Mathematical Formula 11]

$$F_D = \frac{1}{2}\rho V^2 C_D A \quad (1)$$

Furthermore, in the case when the gas can be deemed as an ideal gas, the ideal gas law shown in the following mathematical formula (2) is established among the pressure P of the gas, the molecular weight M, the density ρ of the gas, a gas constant R, and the temperature T of the gas:

[Mathematical Formula 12]

$$PM = \rho RT \quad (2)$$

Therefore, by deleting ρ from the mathematical formulas (1) and (2), the following mathematical formula (3), which shows the relationship between the drag force $F_D$ and the molecular weight M, is obtained:

[Mathematical Formula 13]

$$F_D = \frac{PV^2 C_D A}{2RT} M \quad (3)$$

It is understood from the mathematical formula (3) that the drag force $F_D$ applied by a gas flow relates to the molecular weight of the gas.

In the molecular weight measurement method of the present invention, since a value of the drag force $F_D$ applied by the gas flow is provided by measuring the mechanical deformation of the structure caused by the gas flow, it becomes possible to obtain the molecular weight M of the gas. At this time, values preset are used or the values are measured as needed for other variable numbers, specifically for the values of the pressure P of the gas, the temperature T of the gas, the relative velocity V of the gas and the drag coefficient $C_D$, whereby the molecular weight M of the gas can be determined.

The drag coefficient $C_D$ is a non-dimensionalized value of the drag force $F_D$ using a dynamic pressure and a surface area A, and is varied by the shape (angle of attack) of the structure against the flow of the fluid, the viscosity of the fluid, the velocity of the flow (Reynolds number) and a Mach number. Therefore, an appropriate value can be determined by presetting these conditions, or measuring these conditions as needed.

In the molecular weight measurement method of the present invention, the deformation amount of the structure can be measured by a known deformation measurement means. Specifically, the deformation measurement means is an apparatus that can measure an amount of deformation such as deformation of the structure, and various means that have been used in conventional nanomechanical sensors can be applied. Specifically, for example, devices including surface stress sensors, other elements that convert mechanical deformation or stress to an electric signal (for example, a piezoresistive element), devices configured to reflect laser light at a surface of a structure and measure the reflected light, optical reading devices including an interferometer and a holographic microscope, piezoelectric elements or field effect transistors, or devices configured to read a change in electrostatic capacity, and the like can be preferably exemplified.

In the molecular weight measurement method of the present invention, the structure is not specifically limited as long as it causes a mechanical deformation or a change in optical, electric and magnetic properties by the collision of a gas, and any object can be used, and for example, a slice-shaped element supported at one or plural portion(s) can be preferably exemplified. More specifically, in the present invention, as shown in FIG. 1, a cantilever made of silicon can be preferably exemplified. When a flow of a gas sample is applied to such structure, the cantilever deforms (deflects) by the collision of the molecules of the gas sample. The deformation amount (deflecting amount) is determined by parameters such as the flow rate of the gas, and the molecular weight of the gas molecule. Furthermore, as other structures, for example, structures having various forms such as slice-shaped-objects supported at two or more portions such as a double-supported beam, a film body, and the like can be adopted.

The method and means for allowing the gas to impinge on the structure are not specifically limited, and an embodiment in which the gas is flowed or blasted to the structure to cause collision, and an embodiment in which the structure is moved in the gas to allow the gas to impinge on the structure can be preferably exemplified. In this case, the relative velocity V of the gas with respect to the structure is, for example, the velocity of the gas (air flow) in the case of the embodiment in which the gas is flowed to the structure to cause collision, or the velocity of the movement of the structure in the case of the embodiment in which the structure is moved in the gas to allow the gas to impinge on the structure.

The case when the gas impinges on the structure in the form of a jet flow will be discussed hereinbelow.

It is known that a velocity of a jet flow, which has a symmetrical shape in the three-dimensional axis direction, is provided by the following mathematical formula:

[Mathematical Formula 14]

$$V = \frac{3}{8\pi}\left(\frac{K}{vH}\right)\frac{1}{\left[1+\left(\frac{1}{4}\right)\xi^2\right]^2} \quad (4)$$

wherein $$\xi = \frac{1}{4}\sqrt{\frac{3}{\pi}}\frac{\sqrt{K}}{v}\frac{x}{H}, K = \frac{J}{\rho}, v = \frac{\mu}{\rho}.$$

Herein the mathematical formula (4) is substituted to V in the mathematical formula (3), and A=w×L is further substituted, whereby the following mathematical formula (5) is obtained:

[Mathematical Formula 15]

$$F_D = \frac{9wC_D LM^3 P^3 Q^4}{8\pi^4 \mu^2 l^4 H^2 R^3 \left(\frac{3x^2 M^2 P^2 Q^2}{16\pi^2 \mu^2 l^2 H^2 R^2 T^2} + 1\right)^4 T^3} \quad (5)$$

The above-mentioned formula provides a force $F_D$, which is generated in the case when a gas having a molecular weight M, a pressure P, a temperature T and a dynamic viscosity coefficient μ is flowed at a flow rate Q as an axisymmetric laminar jet from a pipe having a diameter l, and impinges on an object having a width w and a length L placed at a distance H from an outlet at a drag coefficient $C_D$. x represents a distance from the center point of the outlet in the direction perpendicular to the jet flow axis.

The object subjected by the drag force $F_D$ can be any one, and this is not limited to a cantilever as a matter of course. Furthermore, since the magnitude of the drag force $F_D$ is determined by the distance x from the jet flow axis, the mathematical formula (5) is valid if the object that is subjected to the drag force $F_D$ is placed on any place with respect to the jet flow.

It should be noted that the drag coefficient $C_D$ in the mathematical formula (5) is not a constant but a function of x. Since the dragcoefficient $C_D$ is a value having a correlation with a Reynolds number (Re=ρV(x)l/μ), the value changes depending on V(x), i.e., x. This is intuitively explained as follows. The position on the jet flow axis (x=0), i.e., the center of the jet flow, and the position apart from the jet flow (x>0 or x<0) are different in value of the flow velocity V(x) of the gas, and thus the Reynolds number, which is a ratio of a viscous force and an inertia force, differs depending on such difference; therefore, the fluid mechanical property of the gas differs, and the coefficient $C_D$ of the subjected force differs.

The molecular weight measurement method of the present invention will further be explained below in detail, including consideration on the Euler-Bernoulli theory, with adding the condition that the gas impinges on the structure in the form of a jet flow in the molecular weight measurement method of the present invention, and the condition that the structure on which a gas sample to be measured is allowed to impinge in the form of a jet flow is a cantilever as exemplified in FIG. 1, i.e., the condition that a cantilever such that the position of the free end is adjusted to a position on the jet flow axis (x=0), and the length direction is directed to the x-axis direction is utilized as the object that is subjected to the drag force $F_D$.

As is well-known, a deformation amount z of the cantilever when a distributed one-dimensional load (q=$F_D$/L) is applied to a cantilever having a length L, a Young's modulus E, a second moment of area I is provided by the following differential equation.

[Mathematical Formula 16]

$$EI \frac{d^4 z}{dx^4} = q = \frac{F_D}{L} \quad (6)$$

As is also well-known, a second moment of area (I) of a cantilever having a rectangular cross-section is represented by the following mathematical formula (7) by using a width w of the cantilever and a thickness t of the cantilever:

[Mathematical Formula 17]

$$I = \frac{wt^3}{12} \quad (7)$$

The free end of the cantilever is adjusted to the center of the jet flow, and the cantilever is placed above the outlet of the jet flow (FIG. 1). x in the mathematical formula (6) varies from 0 (the free end) to L (the fixed end).

The mathematical formula (5) that represents $F_D$ is substituted to the mathematical formula (6), and integrated four times. Integration constants that appear at this time are determined based on the following boundary conditions.

Boundary condition 1: At the free end (x=0), the shear force is zero, i.e., the third-order differentiation of z is zero.

Boundary condition 2: At the free end (x=0), the bending moment is zero, i.e., the second-order differentiation of z is zero.

Boundary condition 3: At the free end (x=L), the deflection angle is zero, i.e., the first-order differentiation of z is zero.

Boundary condition 4: At the fixed end (x=L), the deflection is zero, i.e., z is zero.

Integration is conducted four times and an integration constant is determined by this way, whereby the drag force $F_D$ can be obtained.

However, the problem herein is that, as shown in the mathematical formula (5), the drag force $F_D$ includes the drag coefficient $C_D$, and this drag coefficient $C_D$ is a value having a correlation with the Reynolds number Re (=ρV(x) l/μ; i.e., the point is that Re is a function of V(x), that is, a function of x), and thus the drag coefficient $C_D$ is a function of x. That is, when the mathematical formula (6) is integrated by x, the drag coefficient $C_D$ in the drag force $F_D$ on the right is also integrated by x. Therefore, the solution of the integration of the mathematical formula (6) cannot be obtained as long as the drag coefficient $C_D$ is defined as a function of x. Therefore, for example, when such function of $C_D$ is experimentally obtained, then a mathematical formula for obtaining the molecular weight of the sample gas can be derived from the displacement of the cantilever.

An example of a means for obtaining the drag coefficient $C_D$ as such function of x is shown below.

Herein, an analytical relationship of $C_D$ and Re, which is an approximate relationship established with a measurement embodiment of "jet flow" together with "cantilever" is introduced under the conditions of Examples, is introduced.

Firstly, a general definition of a Reynolds number is provided by the following formula:

[Mathematical Formula 18]

$$Re = \frac{\rho V l}{\mu} \quad (8)$$

In the formula, ρ represents a density of a gas, V represents a flow velocity of the gas, l represents a representative length (a diameter of a pipe from which the gas is released, or the like, the details are mentioned below), and μ represents a dynamic viscosity coefficient. It should be noted that, since the condition herein is a jet flow, V is a function of x. Furthermore, it was found from the experimental results that the relationship between the drag coefficient $C_D$ and the Reynolds number Re is approximately provided as follows:

[Mathematical Formula 19]

$$C_D = \frac{\alpha}{\sqrt{Re}} \quad (9)$$

Specifically, it was found that, in confirming the consistency with the experimental values by changing the index relating to Re, when the index is set as −0.5 as in the mathematical formula (9), "linear relationship between the molecular weight and deflection (strictly an approximately linear relationship)" confirmed in this Example is reproduced at a high accuracy.

The value of a was determined based on a value of $C_D$ obtained from experiments based on the mathematical formula (3) and the like, and a value of Re obtained from the mathematical formula (8) based on the values of V(x) and the like obtained from a calculation and a finite element analysis. The value of a varies depending on the value utilized as the representative length l. In the case when a fluid in the pipe is considered, it is reasonable to utilize the diameter of the pipe as a representative length, and when l is deemed as the diameter of the pipe, the value of a is about 9.21 (in the case when α is calculated based on the value of V obtained from a finite element analysis), or about 10.2 (in the case when α is calculated based on the value of V obtained from an analytical solution of a jet flow). On the other hand, it is considered that it is sufficiently appropriate to adopt the length of an object on which the gas impinges, if l is set as a width of the cantilever w, then the value of α is approximately about 5.6 (in the case when α is calculated based on the value of V obtained from an analytical solution of a jet flow).

Since the drag coefficient $C_D$ can be defined as a function of x, $C_D$ is substituted to the mathematical formula (5), and the obtained drag force $F_D$ is substituted to the mathematical formula (6) and integrated four times, and integration constants are determined from the boundary conditions, whereby the following mathematical formula (10) is obtained.

[Mathematical Formula 20]

$$z(x) = \left[-16\pi^2 \alpha \mu^2 l^2 wxH^2[\mathrm{atan}(\beta L) - \mathrm{atan}(\beta x)]R^2T^2 - \right. \\ 4\sqrt{3}\,\pi\alpha\mu lwxH(x-L)MPQRT - \\ \left. 3\alpha w\{(3x-2L)L^2\mathrm{atan}(\beta L) - x^3\mathrm{atan}(\beta x)\}M^2P^2Q^2\right] \Big/ \\ \left[2^{9/2}\pi^2 l^{5/2}E\sqrt{H}\,IMPRT\right] \tag{10}$$

wherein $$\beta = \frac{\sqrt{3}\,MPQ}{4\pi\mu lHRT}.$$

By assigning x=0 to this mathematical formula, the following formula, which represents a deflection on the jet flow axis and in the case of the free end of the cantilever, is obtained:

[Mathematical Formula 21]

$$z(0) = \frac{3\alpha wL^3\mathrm{atan}(\beta L)MPQ^2}{2^{7/2}\pi^2 l^{5/2}E\sqrt{H}\,IRT} \tag{11}$$

When the values in Table 7 and α=9.21 are assigned to this formula, the following mathematical formula is obtained:

[Mathematical Formula 22]

$$z(0) = 2.70 \times 10^{-5}\,M\,\mathrm{atan}(1.14 \times 10^2(M)) \tag{12}$$

This formula indicates that the former half part represents linearity against the molecular weight M, and the latter atan part provides perturbation to the linearity in the former half part.

Since the unit of M in the mathematical formula (12) is kg/mol, the unit is converted to g/mol, which is generally used for the case when a molecular weight is represented, and set as $M_g$, whereby the following mathematical formula is obtained:

[Mathematical Formula 23]

$$z(0) = 2.70 \times 10^{-8}\,M_g\,\mathrm{atan}(1.14 \times 10^{-1}\,M_g) \tag{13}$$

Figure 2:
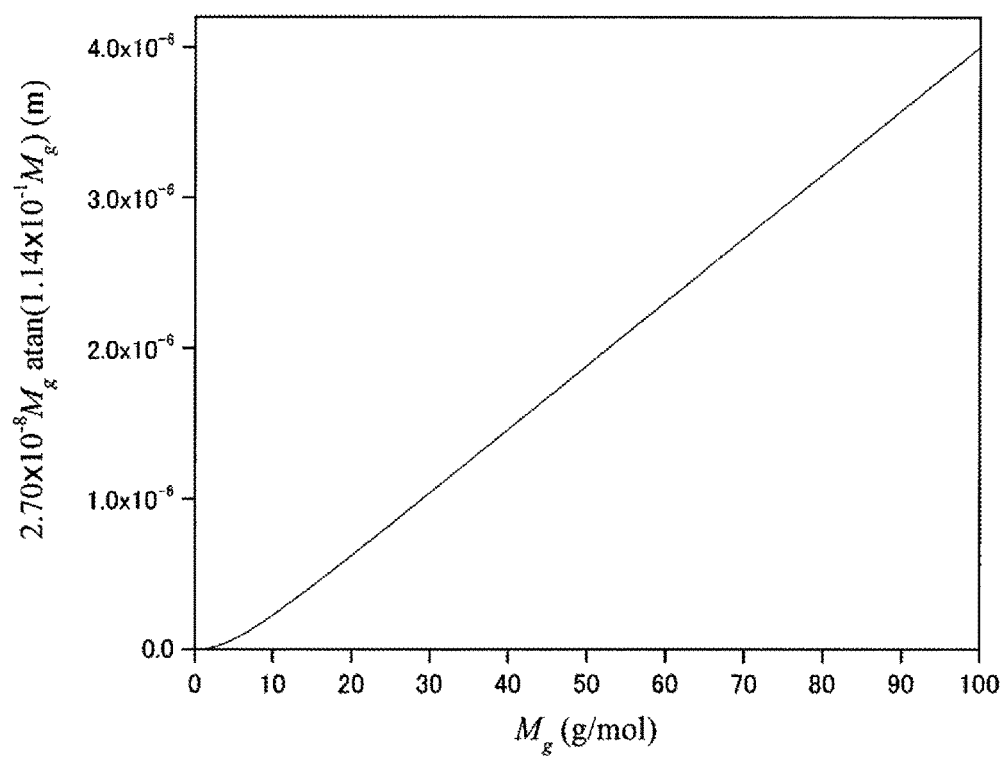
FIG. 2 is a graph showing the formula relating the molecular weight to the deformation amount of a cantilever, which is a result obtained by solving a differential equation showing the principle of the molecular weight measurement device of the present invention based on the conditions and measurement results of the Examples.
Figure 3:
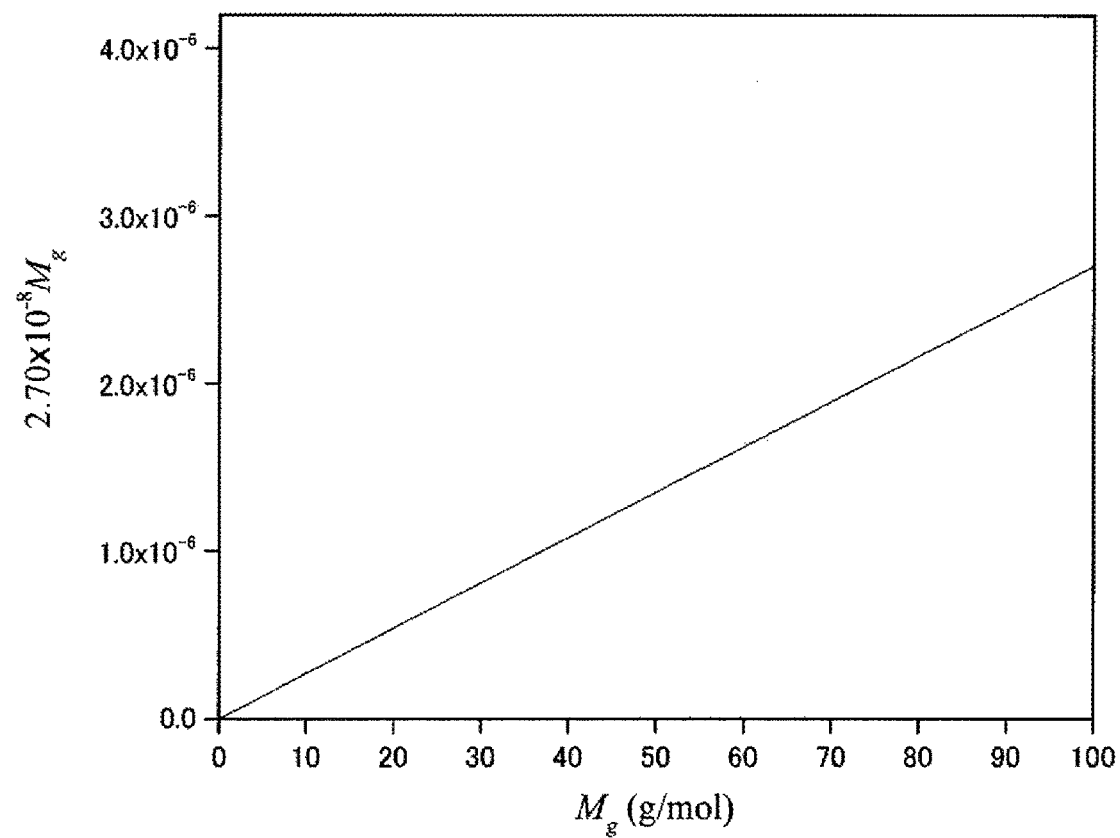
FIG. 3 is a graph showing the linear elements of the functions of the above-mentioned relational formula.
Figure 4:
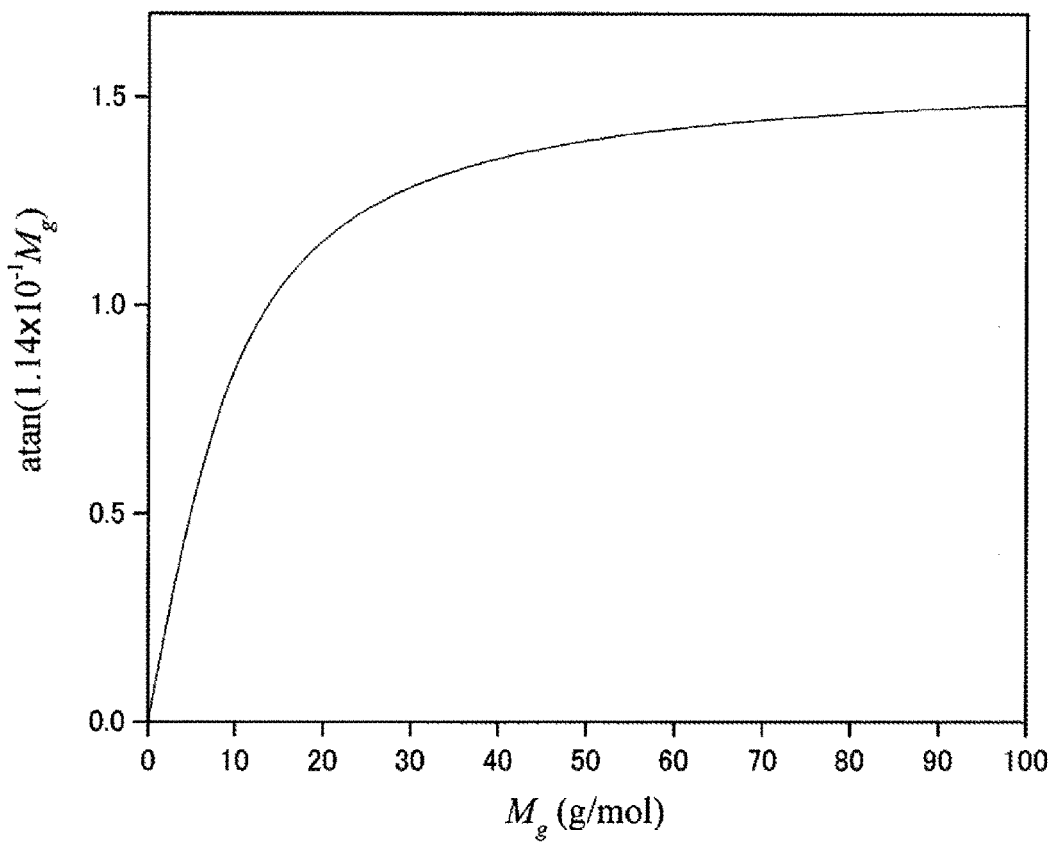
FIG. 4 is a graph showing the perturbation elements of the functions of the above-mentioned relational formula.

This mathematical formula is plotted against the molecular weight $M_g$ [g/mol] as shown in FIG. 2. As is apparent from FIG. 2, this mathematical formula is approximately linear, but the linearity collapses especially at a low molecular weight region. Furthermore, graphs in which the former half part, which is the linear element, and the latter half part, which is the non-linear element, of this mathematical formula are respectively shown in FIGS. 3 and 4. As a matter of course, FIG. 3 is a linear graph. The atan part provides perturbation to this linear relationship. When the value of this perturbation amount is 1, the graph is completely linear. The perturbation amount becomes significantly lower than 1 and deviates from linearity especially at the low molecular weight region. The high molecular weight region tends to be saturated at a value of about 1 to 1.5, and thus does not significantly affect the linearity, whereas non-linear perturbation is added to the deflection amount of the cantilever with respect to the molecular weight $M_g$. When the atan part is corrected, it becomes possible to properly provide the deflection amount of the cantilever with respect to the molecular weight $M_g$.

As mentioned above, the value of the Reynolds number Re varies depending on the part of the gas to be focused on. For example, in the case when the gas in the pipe is focused on, the diameter of the pipe is generally utilized as l that provides the Reynolds number Re in the mathematical formula (8). The Reynolds numbers (Re) calculated by the mathematical formula (8) in this case are summarized in Table 9. On the other hand, in the case when the gas in the periphery of the cantilever is focused on, the width of the cantilever is generally utilized as l. The Re calculated by the mathematical formula (8) in this case are summarized in Table 10. Therefore, according to the mathematical formula (8), the Reynolds number Re varies depending on the value of l, and as a result, the value of α also varies according to the mathematical formula (9). For example, in the case when the gas in the pipe and the gas in the periphery of the cantilever are focused on, the values of a are about 9 and 5, respectively. Therefore, since the Reynolds number Re varies depending on the gas to be focused on in such way, it should be noted that FIG. 16 also changes in accordance with this variation. Furthermore, it should also be noted that the mathematical formula (9) also changes depending on the conditions of the experiment and the range of the Reynolds number of the gas to be focused on. The Reynolds number Re is a value provided by the mathematical formula (8), whereas the drag coefficient $C_D$ is an experimentally obtained value, and these Re and $C_D$ generally have a complex relationship. As an example, the relationship between Re and $C_D$ in the case of a sphere is introduced in Non-patent Literature 3. Therefore, the mathematical formula (9) is a relationship that is approximately established, consistently under the conditions of the present Example and in the case when the Reynolds number is limited to be in a predetermined range, and in the case when the conditions are changed, it is necessary to confirm the relationship between Re and $C_D$ in accordance with the change in advance. However, in a region that provides not a turbulent flow in which irregular fluctuation occurs but a laminar flow that enables an appropriate measurement (a region equal to or less than the critical Reynolds number, approximately Re<$10^3$), Re and $C_D$ have a predetermined relationship in many cases; therefore, the relationship between Re and $C_D$ can be described by the mathematical formula (9) of a format based on the mathematical formula (9) in an actual measurement environment.

In the molecular weight measurement method of the present invention, for example, by calibrating the relationship between the molecular weight M of the gas and the deformation amount z of the cantilever in advance by using a standard gas, it becomes possible to obtain the molecular weight M of the gas sample directly from the measured value of the deformation amount z of the cantilever at high accuracy. If it is possible to conform the parameters such as a relative velocity V of the gas, a pressure P of the gas and a temperature T to the parameters of the gas sample in advance (or put these parameters into ranges such that the measurement results are within required error ranges) during the calibration using a standard gas, then it is unnecessary to obtain the values of these parameters by specific measurements and the like.

In the molecular weight measurement method of the present invention, the gas to be measured can be a mixed gas containing plural kinds of molecules. In this case, in the process of obtaining the molecular weight of the gas, an average molecular weight of the molecules in the mixed gas can be obtained. Furthermore, in the molecular weight measurement method of the present invention, a molecular weight of a liquid sample or a solid sample can also be measured by vaporizing the liquid sample or solid sample, and allowing the gas state sample to impinge on a structure such as a cantilever.

In the above, an ideal gas is supposed in the molecular weight measurement method according to the present invention, and the ideal gas excludes the contribution of the volumes of the molecules themselves and the van der Waals force. In a precise sense, it is necessary to argue over a real gas for which the contribution of these is considered. Therefore, the effects of the above-mentioned parameters are mentioned here in a quantitative way.

The van der Waals equation is represented by the following form:

[Mathematical Formula 24]

$$\left(P + \frac{an^2}{V_{gas}^2}\right)(V_{gas} - nb) = nRT \tag{14}$$

In the formula, P represents a pressure of the gas, $V_{gas}$ represents a volume of the gas, n represents a number of moles of the gas, R represents a gas constant, T represents a temperature of the gas, and a and b represent van der Waals constants of the gas. The van der Waals constants are values that are inherent to each gas, and typical values are shown in Table 2.

TABLE 2

|   | He | $N_2$ | Air | Ar | $CO_2$ |
|---|---|---|---|---|---|
| a | 0.0340 | 1.39 | 1.33 | 1.35 | 3.60 |
| b | 0.0238 | 0.0392 | 0.0366 | 0.0322 | 0.0428 |

A volume of 1 mol of gas at 25° C. can be obtained from the mathematical formula (14) based on the values in Table 2. Table 3 shows the volumes of helium, nitrogen, air, argon and carbon dioxide at 1 atm.

TABLE 3

| Pressure | Molecular volume (L) | | | | | |
|---|---|---|---|---|---|---|
| (atm) | He | $N_2$ | Air | Ar | $Co_2$ | Ideal gas |
| 1.0 | 24.501 (0.094%) | 24.461 (−0.069%) | 24.460 (−0.074%) | 24.455 (−0.094%) | 24.373 (−0.43%) | 24.478 |

The molar volume of the ideal gas can be obtained as 24.478 L from the ideal gas law. As is understood from Table 2, the molecular volumes of the respective gases and the volume of the ideal gas are approximately identical, and even in the case of carbon dioxide, which gives the largest deviation, the difference is only about 0.5% or less. Therefore, regarding measurements conducted at around 25° C. and 1 atm, it is possible to apply the argument on the premise of an ideal gas within this error range.

As another factor that affects the measurement results, a Joule-Thomson effect may be exemplified. Generally, a phenomenon that, when a gas passes through a porous wall or the like, in the case when the pressures before and after the wall are kept constant, the temperature of the gas after the passage decreases, is known as a Joule-Thomson effect. Therefore, for example, in a molecular weight measurement device having a form such that a gas is flowed from an outlet having a small diameter to a broad space, it is necessary to consider the contribution of the Joule-Thomson effect.

The object to which the Joule-Thomson effect is applied is a compressible fluid, and the compressible fluid is defined by the magnitude of a Mach number. The Mach number Ma is represented by the following mathematical formula (15).

[Mathematical Formula 25]

$$Ma = \frac{v_f}{v_s} \tag{15}$$

In the formula, $v_f$ represents a velocity of a fluid, and $v_s$ represents a speed of sound. The speed of sound varies depending on a surrounding medium, and is provided by the following mathematical formula (16).

[Mathematical Formula 26]

$$v_s = \sqrt{\frac{\gamma RT}{M}} \tag{16}$$

In the formula, γ represents a heat capacity ratio of the gas, R represents a gas constant, T represents a temperature of the gas, and M represents a molecular weight of the gas. Table 4 shows the values of $\gamma$ and M of helium, nitrogen, air, argon and carbon dioxide.

TABLE 4

|  | He | $N_2$ | Air | Ar | $CO_2$ |
|---|---|---|---|---|---|
| $\gamma$ | 1.66 | 1.40 | 1.40 | 1.67 | 1.29 |
| M (g/mol) | 4.003 | 28.01 | 28.97 | 39.95 | 44.01 |

The speeds of the sound and Mach numbers in the respective gases obtained from the values shown in Table 4 and the mathematical formula (16) are shown in Table 5. As the flow velocity of the gas herein, a value (about 1.41 m/s) calculated assuming a pipe with a diameter of 300 μm and a flow amount of 6 mL/min was used.

TABLE 5

|  | He | $N_2$ | Air | Ar | $CO_2$ |
|---|---|---|---|---|---|
| $v_s$ (m/s) | 970 | 337 | 331 | 308 | 258 |
| Ma | 0.00146 | 0.00420 | 0.00428 | 0.00460 | 0.00549 |

If the Mach number is greater than 0.3, then the gas is defined as a compressible gas. Therefore, the velocity $v_f$ of the gas when the Mach number is 0.3 is calculated as shown in Table 6.

TABLE 6

|  | He | $N_2$ | Air | Ar | $CO_2$ |
|---|---|---|---|---|---|
| $v_f$ (m/s) | 291 | 101 | 99 | 92 | 77 |

If $v_f$ is less than the value in Table 6, then it is possible to handle the gas as a non-compressible gas. Therefore, in this case, the above-mentioned effect of the Joule-Thomson effect can be neglected.

Secondly, an exemplary embodiment of the molecular weight measurement device of the present invention will be explained.

The molecular weight measurement device of the present invention includes:

a chamber having an inlet from which a gas is introduced, and having a cantilever placed in the chamber;

a gas feeding means configured to feed a gas from the inlet into the chamber to allow the gas to impinge on the cantilever;

a deformation measurement means configured to measure a cantilever deformation caused by the collision of the gas; and a calculation means configured to calculate a molecular weight of the gas based on the deformation amount of the cantilever.

Figure 5:
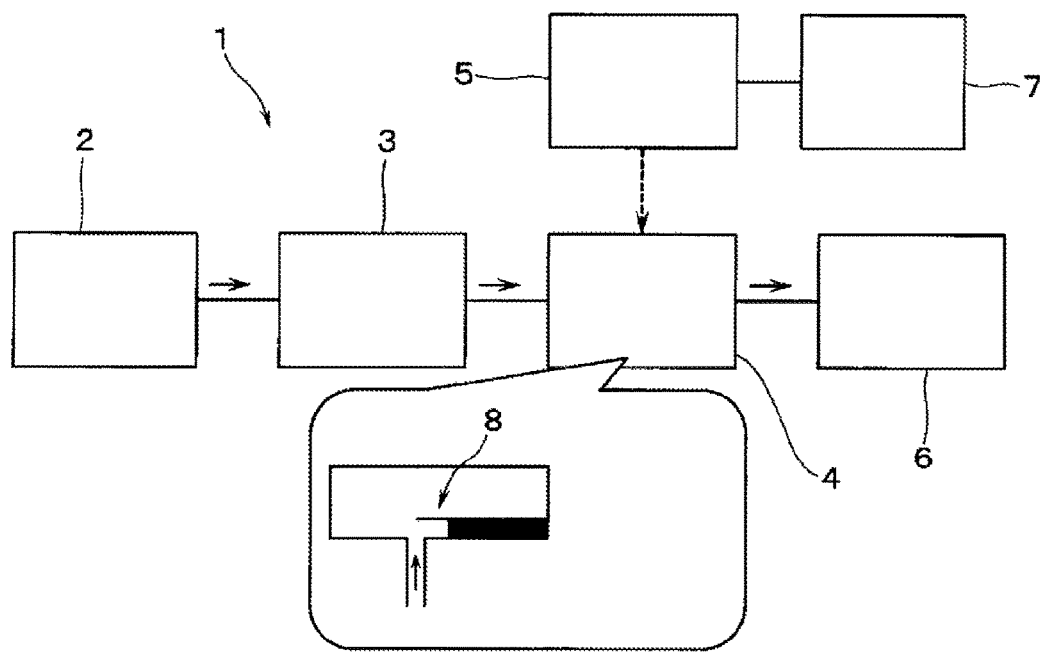
FIG. 5 is a conceptional drawing showing a conceptional structure of an embodiment of the molecular weight measurement device of the present invention.

FIG. 5 is a schematic drawing exemplifying an exemplary embodiment of the molecular weight measurement device of the present invention.

The molecular weight measurement device 1 of this exemplary embodiment includes a gas feeding means 2, a flow amount controlling means 3, a chamber 4, a deformation measurement means 5, a flow amount measurement means 6, and a calculation means 7.

The specific constitution of the gas feeding means 2 is not specifically limited, and for example, a pump that can feed a gas at a flow velocity within the range of about 1 μL/min to 1 kL/min, preferably a flow velocity within the range of 3 mL/min to 35 mL/min, and the like can be exemplified.

The flow amount controlling means 3 is placed between the gas feeding means 2 and the chamber 4. The flow amount controlling means 3 may be any one that can adjust and control the flow amount of the gas fed from the gas feeding means 2, and the specific constitution is not specifically limited.

The chamber 4 contains a cantilever 8. The cantilever 8 is not specifically limited as long as it is a cantilever that causes a change in property including mechanical deformation, or optical, electric or magnetic change by collision with the gas, and the length, width, Young's modulus, thickness and the like of the cantilever 8 can be suitably preset. Specifically, for example, as the cantilever 8, cantilevers made of optional materials such as organic, inorganic and bio-derived substances; for example, cantilevers made of silicon, polymer, paper and the like, can be selected. In response to this, the Young's modulus can be optionally selected within the range of about 1 Pa to 1 PPa (1,000,000, 000,000,000 Pa), and the Poisson's ratio can also be optionally selected within the range of about −1 to 0.50. Furthermore, the length, width, thickness and the like can be optionally selected within the range of 1 nm to 1 km. For the shape of the cantilever 8, in either of the length, width and thickness directions, a length, width or thickness in which a part or entirety thereof has optional angle and curvature can be selected. Similarly, for the cross-sectional surface shape of the cantilever 8, an optional shape such as a rectangular shape, a star shape, a polygonal shape or a circular shape, or a shape in which a part of or all sides is constituted by curves can be selected.

The shape and the like of the gas inlet of the chamber 4 are also not specifically limited, and may have a cross-section of a circular shape, a rectangular shape or the like. Furthermore, the size of the inlet can be suitably designed, and for example, in the case when the inlet has a cross-section of a circular shape, the diameter of the inlet can be optionally selected within the range of about 1 nm to 1 km.

As the deformation measurement means 5, a deformation amount of the cantilever 8 in the chamber can be measured. Specifically, as the deformation measurement means 5, devices such as a surface stress sensor, other devices that convert a mechanical deformation or stress to an electric signal (for example, a distortion gauge and a piezoresistive element, or devices configured to measure electric properties including electric capacity, surface electric charge and dielectric property, devices configured to measure any change in optical properties and magnetic properties, and the like), a device configured to reflect a laser light on a surface of a structure and measure the reflected light, optical reading devices including an interferometer and a holographic microscope, and a piezoelectric element or a field effect transistor, can be exemplified.

The flow amount measurement means 6 is placed downstream of the chamber. The specific constitution of the flow amount measurement means 6 is not specifically limited, and a known device that can measure the flow amount of a gas sample fed into the chamber can be suitably used.

As the calculation means 7, a calculation means that is configured to calculate the molecular weight M of the gas by substituting measured numerical values or preset numerical values to the respective parameters of the following mathematical formula (17), which shows the relationship between the deformation amount z of the cantilever 8 and the molecular weight M of the gas, can be exemplified.

[Mathematical Formula 27]

$$z(x) = \left[-16\pi^2\alpha\mu^2 l^2 wxH^2\{\mathrm{atan}(\beta L) - \mathrm{atan}(\beta x)\}R^2 T^2 - \right.\quad(17)$$
$$4\sqrt{3}\,\pi\alpha\mu lwxH(x-L)MPQRT -$$
$$\left.3\alpha w\{(3x-2L)L^2\mathrm{atan}(\beta L) - x^3\mathrm{atan}(\beta x)\}M^2 P^2 Q^2\right]\Big/\Big[$$
$$2^{9/2}\pi^2 l^{5/2} E\sqrt{H}\,IMPRT\Big]$$

wherein $$\beta = \frac{\sqrt{3}\,MPQ}{4\pi\mu lHRT}.$$

In the above-mentioned formula, α represents a constant determined by experimental conditions, and is about 9 at this time but is actually a constant in the range from −10000 to 10000, μ represents a dynamic viscosity coefficient, l represents a diameter of a pipe, w represents a width of the cantilever, H represents a distance from the center point of the inlet in the jet flow axis direction, P represents a pressure of the gas, Q represents a flow rate, R represents a gas constant, T represents a temperature of the gas, x represents a distance from the center point of the inlet in the direction perpendicular to the jet flow axis, and L represents a length of the cantilever. In addition, as mentioned above, in the case when the gas in the periphery of the cantilever is focused on, there are some cases when l is preferably a width w of the cantilever. In this case, the values of the Reynolds number and the above-mentioned constant α of the focused on gas also change in accordance with the width w.

According to the molecular weight measurement device of the present invention 1, the molecular weights of almost all gases and mixed gases thereof can be measured although the device is simple and small. Furthermore, if a deflection amount or a stress generated by the deflection is continuously measured, it becomes possible to measure a molecular weight in real-time.

Accordingly, since the device can be miniaturized according to the molecular weight measurement device 1 of the present invention, anybody can easily measure molecular weight of a gas anytime and anywhere, for example, it becomes possible to measure a change in environments and the like by moving a structure in a space containing a gas to be measured. Furthermore, since a molecular weight of a gas can be measured in real-time, the degree of progress of a chemical reaction can be evaluated by observing gas components that are generated during the chemical reaction. In addition, since the device utilizes physical collision of gas molecules, the device can be repeatedly used and the time response is also improved, unlike sensors of a type in which detection is conducted based on adsorption or a chemical reaction.

In conventional nanomechanical sensors mainly utilizing a cantilever, it is necessary to coat the surface of the sensor with a layer that absorbs a specimen molecule. Such a layer is called as a receptor layer (Non-patent Literatures 1 and 2). In this case, it is generally difficult to coat the receptor layer with high reproducibility, since a special technique and the like are required. Furthermore, since the absorption of the specimen molecule by the receptor layer is a phenomenon that includes various interactions including chemical actions, it has a problem that an output from this kind of sensor does not always directly provide a quantified evaluation. Such difficulty relating to the receptor layer is also a problem in other types of sensors than nanomechanical sensors; for example, a quartz crystal microbalance (QCM), a surface plasmon resonance (SPR) or a field effect transistor (FET), or the like. Since the molecular weight measurement device of the present invention does not require such a receptor layer, reproducibility and quantitativity, which are important in practical use, can be achieved easily as compared to other kinds of sensors.

The molecular weight measurement device of the present invention is not limited to the embodiment exemplified in FIG. 5, and can include, for example, other various measurement devices and the like. Furthermore, for example, the flow amount measurement means can also be placed on the upstream side of the chamber. Alternatively, in the case when a mechanism for conducting sample flow such as a pump itself can precisely control the amount of flow, it is also possible to use such a mechanism to provide the information of an amount of the sample flow, without separately providing the means for measuring the sample flow.

Furthermore, the molecular weight measurement device of the present invention can conduct a similar measurement not by a form in which a gas is flowed to a fixed structure, but by a constitution in which a gas is allowed to impinge on a structure by moving the structure itself. For example, a constitution in which a cantilever is rotated around an axis aligned with the fixed end of the cantilever in a tightly-closed chamber or in the atmosphere to allow a gas to impinge thereon, and a deformation amount of the cantilever is read by a piezoresistor or the like can be considered. In this case, since it is not necessary to flow the gas, a pump and a flow meter are also not necessary, and thus the relative velocity between the gas and the structure can be optionally preset by the rotation rate or the moving velocity of the structure, and the like. Furthermore, it also becomes possible to visualize the concentration gradient distribution of the gas sample in a space by moving the outlet of the gas or the cantilever itself in the space, while measuring the deformation amount and the like of the cantilever.

EXAMPLES

<Example 1> Deformation Amount of Cantilever and Gas Molecular Weight (1)

An example of a molecular weight measurement method using the molecular weight measurement device, whose conceptional structure is exemplified in FIG. 5, will be explained below.

In this Example, an experiment was conducted under the conditions shown in Table 7.

TABLE 7

| | | | |
|---|---|---|---|
| Drag coefficient | $C_D$ | — | |
| Drag force | $F_D$ | N | |
| Surface area on which drag force is applied | A | $m^2$ | (w × L) |
| Density of gas | ρ | kg m$^{-3}$ | |
| Relative velocity of gas | V | ms$^{-1}$ | |
| Reynolds number | Re | — | |
| Dynamic viscosity coefficient | μ | Nsm$^{-2}$ | 1.84 × 10$^{-5}$ |

TABLE 7-continued

| | | | |
|---|---|---|---|
| Diameter of pipe | I | m | $300 \times 10^{-6}$ |
| Pressure of gas | P | $Nm^{-2}$ | $1.01 \times 10^{5}$ |
| Molecular weight | M | $kg\ mol^{-1}$ | |
| Gas constant | R | $J\ mol^{-1}\ K^{-1}$ | 8.31 |
| Temperature of gas | T | K | 298 |
| Distance in direction of jet flow axis from center point of inlet | H | m | $450 \times 10^{-6}$ |
| Distance in vertical direction with respect to jet flow axis from center point of inlet | x | m | |
| Axial momentum flux across any plane normal to jet flow axis | J | $kg\ ms^{-1}$ | |
| Young's modulus of cantilever | E | $Nm^{-2}$ | $170 \times 10^{9}$ |
| Second moment of area of cantilever | I | $m^{4}$ | $7.5 \times 10^{-24}$ |
| Deformation of a cantilever | z | m | |
| Length of cantilever | L | m | $500 \times 10^{-6}$ |
| Width of cantilever | w | m | $90 \times 10^{-6}$ |
| Thickness of cantilever | t | m | $1.0 \times 10^{-6}$ |
| Flow rate | Q | $m^{3}s$ | $1.0 \times -10^{-7}$ |

A cantilever made of a silicon having the above-mentioned features was fixed in a small chamber. An inlet and an outlet for a gas sample were made on this chamber. An inlet having a radius of about 150 μm was made right under the cantilever so that a gas sample that comes from the inlet is efficiently flowed to the cantilever. A gas flow meter is connected to the outlet, and a flow rate of the introduced gas was measured. The gas sample was flowed by means of a pump as a gas feeding means.

Using a digital holographic microscope (DHM) having a vertical resolution of 0.2 nm and a real time monitoring capability (this microscope can record a movie at a rate of 10 fps or more) as a deformation measurement means, a deformation amount (deflection) of the cantilever was measured.

Figure 6:
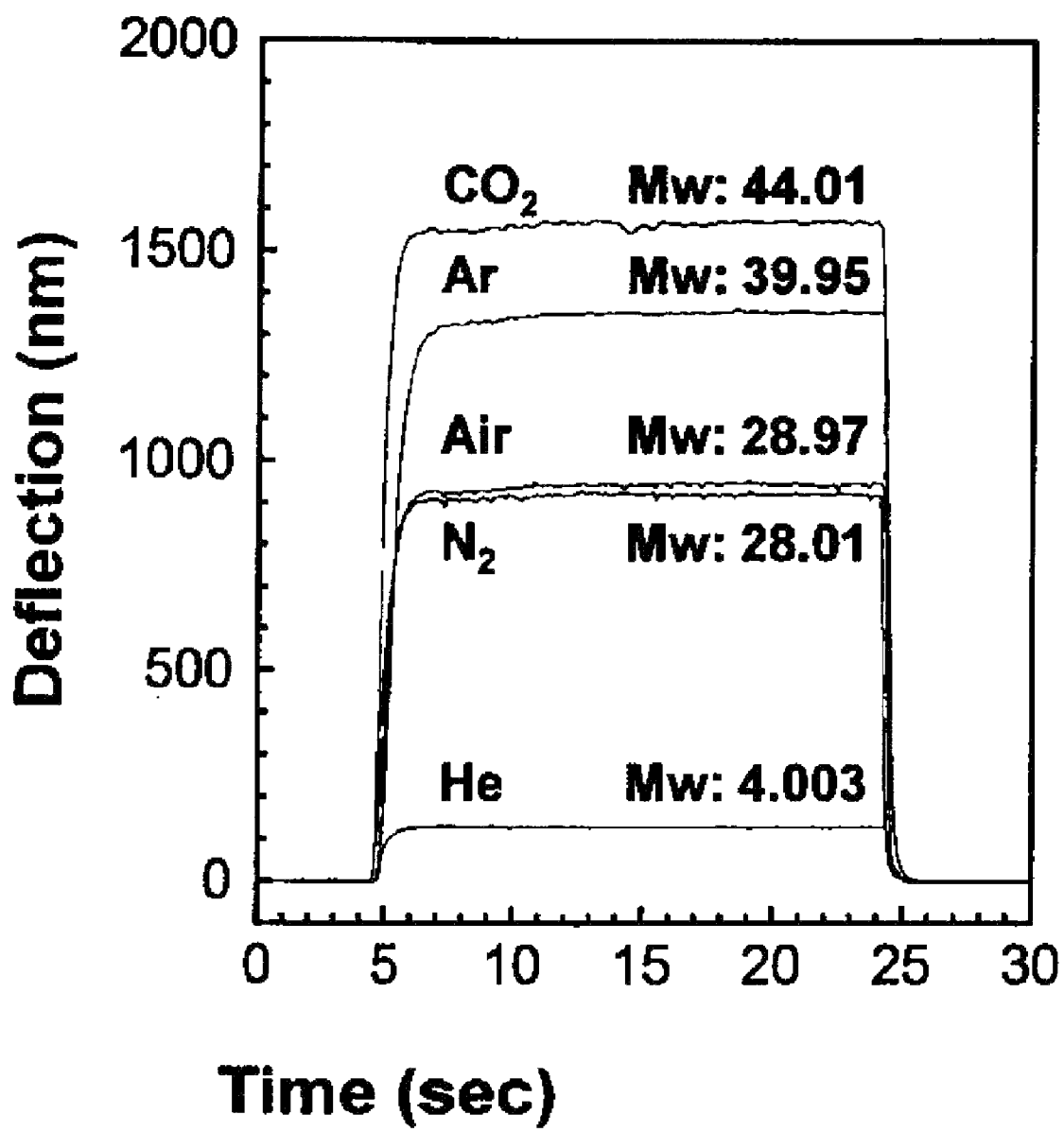
FIG. 6 is a drawing showing the deformation amounts of the cantilever which were observed when various gases were measured by the molecular weight measurement device of an embodiment of the present invention.

Pure helium (molecular weight: 4.003 g/mol), nitrogen (molecular weight: 28.01 g/mol), air (average molecular weight: 28.97 g/mol), argon (molecular weight: 39.95 g/mol) and carbon dioxide (molecular weight: 44.01 g/mol) were each introduced into this chamber at various flow rates, and deformation amounts of the cantilever measured at that time are shown in FIG. 6. It can be confirmed that the deformation amount of the cantilever significantly differs as the molecular weight of the gas or the flow rate of the gas increases.

In addition, in FIG. 6, "rod graph"-like detection outputs were able to be obtained by switching the air flow from the inlet. By turning off the sample flow, the detection output quickly returned to the base line. Accordingly, in the present invention, as long as the sample flow does not induce a permanent deformation to a structure such as a cantilever by the excessively strong force with too high sample flow rate, the effect of the previous sample flow, that is, the gas molecules that have impinged on the structure, does not basically appear in the detection output.

Figure 7:
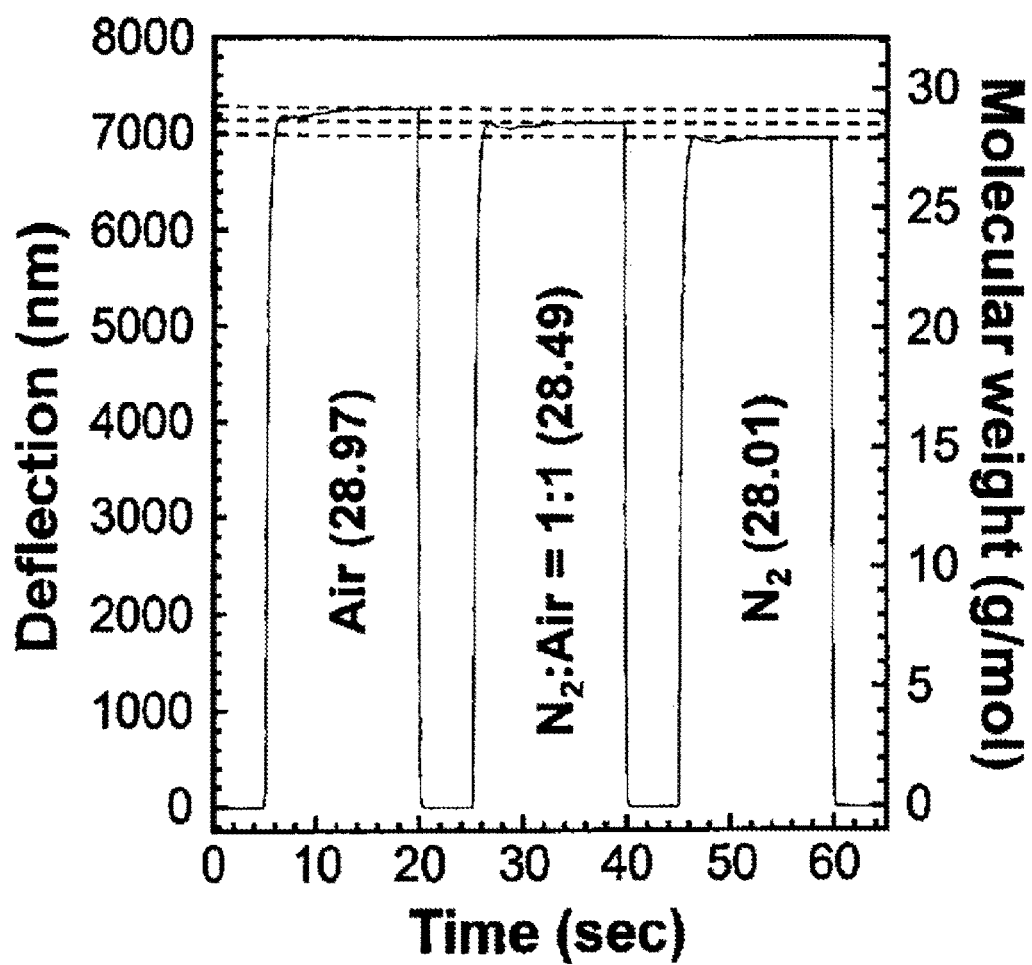
FIG. 7 is a drawing showing the changes in the deformation amount of the cantilever when the mixing ratio of two kinds of gases was varied.

In the present invention, even the gas is a mixed gas, the gas does not affect the measurement principle within a scope in which the gas can be regarded as an ideal gas. Here, the measurement results of cantilever deformations by changing the mixing ratios of the helium and argon, and air and nitrogen are shown in FIG. 7. It was confirmed from these measurement results that the deflection amount (deflection) of the cantilever changes linearly with the mixing ratio. Therefore, in the case of a mixed gas, a deformation amount that corresponds to the average molecular weight of the mixed gas is measured.

It is also possible to monitor a chemical reaction in real-time by observing the gas components that are generated during the chemical reaction by utilizing the method of the present invention. In the case when the molecular weights of the generated gas components are known, the amounts of the generated gases can be also measured quantitatively from the measured deformation amount.

Figure 8:
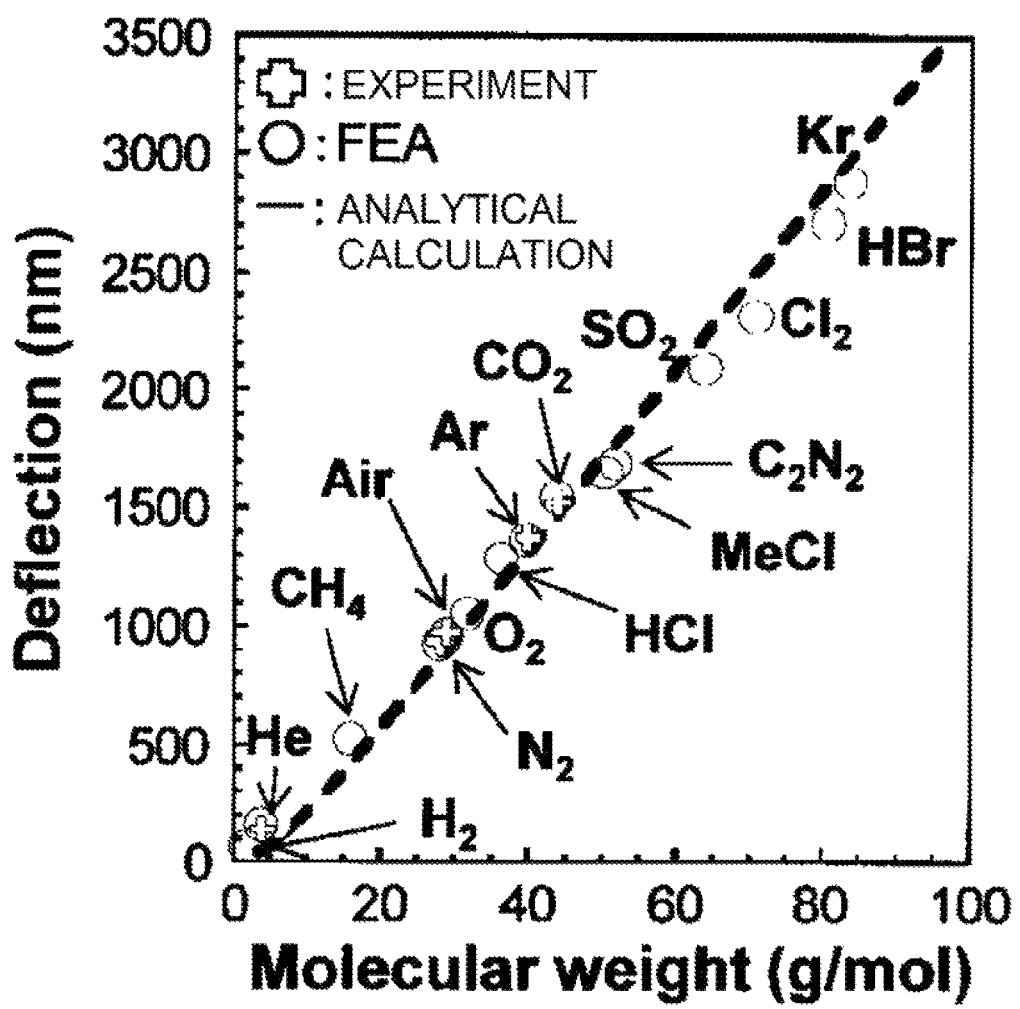
FIG. 8 is a drawing showing the experimental results, and the results of the finite element analysis and analytical calculation.

In FIG. 8, the results of the finite element analysis based on these values using versatile finite element method simulation software COMSOL (registered trademark by COMSOL AB) ("FEA (COMSOL)") and the values obtained in the experiment ("experiment (DHM)") are plotted. In the finite element analysis, a calculation was performed using an elasticity matrix D, taking account of the anisotropy of a single crystal silicon. The elements constituting the elasticity matrix D are $c_{11}$, $c_{12}$, $c_{22}$, $c_{13}$, $c_{23}$, $c_{33}$, $c_{44}$, $c_{55}$ and $c_{66}$, and the corresponding values are 160 GPa, 64 GPa, 160 GPa, 64 GPa, 64 GPa, 160 GPa, 80 GPa, 80 GPa and 80 GPa, respectively. It can be confirmed from FIG. 8 that the measurement results are identical within an error range. Furthermore, the linearity between the molecular weight and the deformation amount (deflection) of the cantilever can be confirmed. By this way, the validity of the working principle of the present invention was verified.

<Example 2> Deformation Amount of Cantilever and Gas Molecular Weight (2)

Gas samples (helium, nitrogen, air, argon and carbon dioxide) were allowed to impinge on a cantilever by utilizing the chamber exemplified in FIG. 5, and the relationship between the deformation amount and the molecular weight of the cantilever was investigated.

The conditions are as shown in the above-mentioned Table 7.

The gas sample was flowed toward the cantilever, and the velocity (V) of the gas sample was measured by a flow rate measurement device, and the velocity (V) of the gas sample was 6 mL/min. The deformation amount of the cantilever was measured by a digital holographic microscope (Digital Holographic Microscope, DHM).

Figure 9:
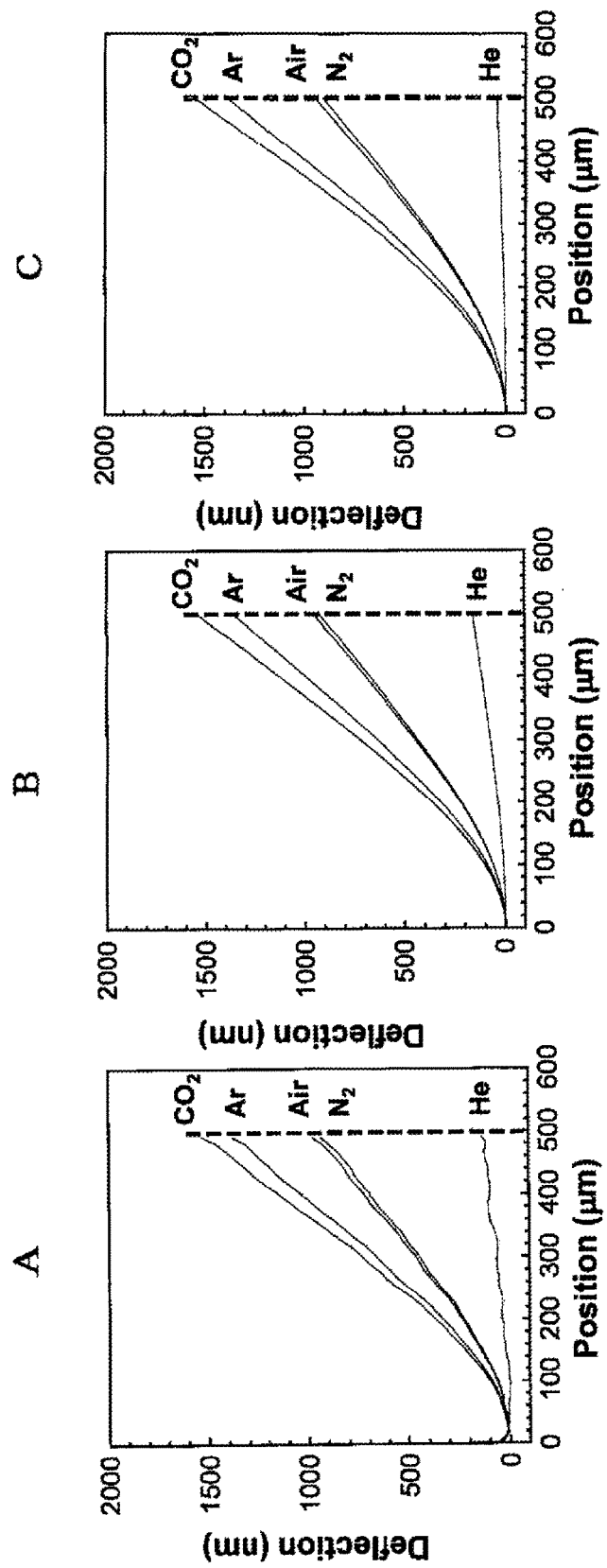
FIG. 9 is a drawing showing the cantilever deformation caused by the collision of the gas sample (helium, nitrogen, air, argon, carbon dioxide) (A: experimental result, B: finite element analysis, C: analytical calculation). The position at 0 μm and the position at 500 μm on the horizontal axis correspond to the fixed end and the free end of the cantilever, respectively. (The definition is different from that of x in the mathematical formulas 2, 6 and 7. In x of the mathematical formulas 2, 6 and 7, the position where x=0 is defined as a free end.)

The results are shown in FIG. 9.

As shown in FIG. 9 (A), the deformation amounts (deflections) of the cantilever for helium, nitrogen, air, argon and carbon dioxide were 138 nm, 937 nm, 978 nm, 1381 nm and 1530 nm, respectively. On the other hand, as shown in FIG. 9 (B), when a finite element analysis (FEA) was conducted by using versatile finite element method simulation software COMSOL (registered trademark by COMSOL AB), the deformation amounts of the cantilever caused by helium, nitrogen, air, argon and carbon dioxide were 123 nm, 971 nm, 1005 nm, 1393 nm and 1536 nm, respectively.

When the above-mentioned deformation amounts were plotted, as shown in FIG. 8, it was confirmed that the molecular weights and the deformation amounts of the cantilever were identical within an error range. Furthermore, the respective parameters shown in Table 7 were substituted to the mathematical formula (17), and the relationship between the deformation amount of the cantilever and the molecular weight was plotted. It can be confirmed that the mathematical formula (17) accurately reproduces the results obtained by the experiments and FEA. Through these results, the validity of the principle of the present invention was verified.

<Example 3> Measurement of Molecular Weight of Liquid Sample

1 μL of a liquid sample (pentane, hexane or heptane) was injected into an oven that had been heated to 150° C., and vaporized. The vaporized sample was then fed to a heated capillary column by using helium as a carrier gas (flow rate: 2.8-2.9 mL/min). The capillary column was connected to a chamber (80° C.) in which a cantilever was placed, and the vaporized sample was fed from the capillary column to the chamber, and then flowed toward the cantilever.

Figure 10:
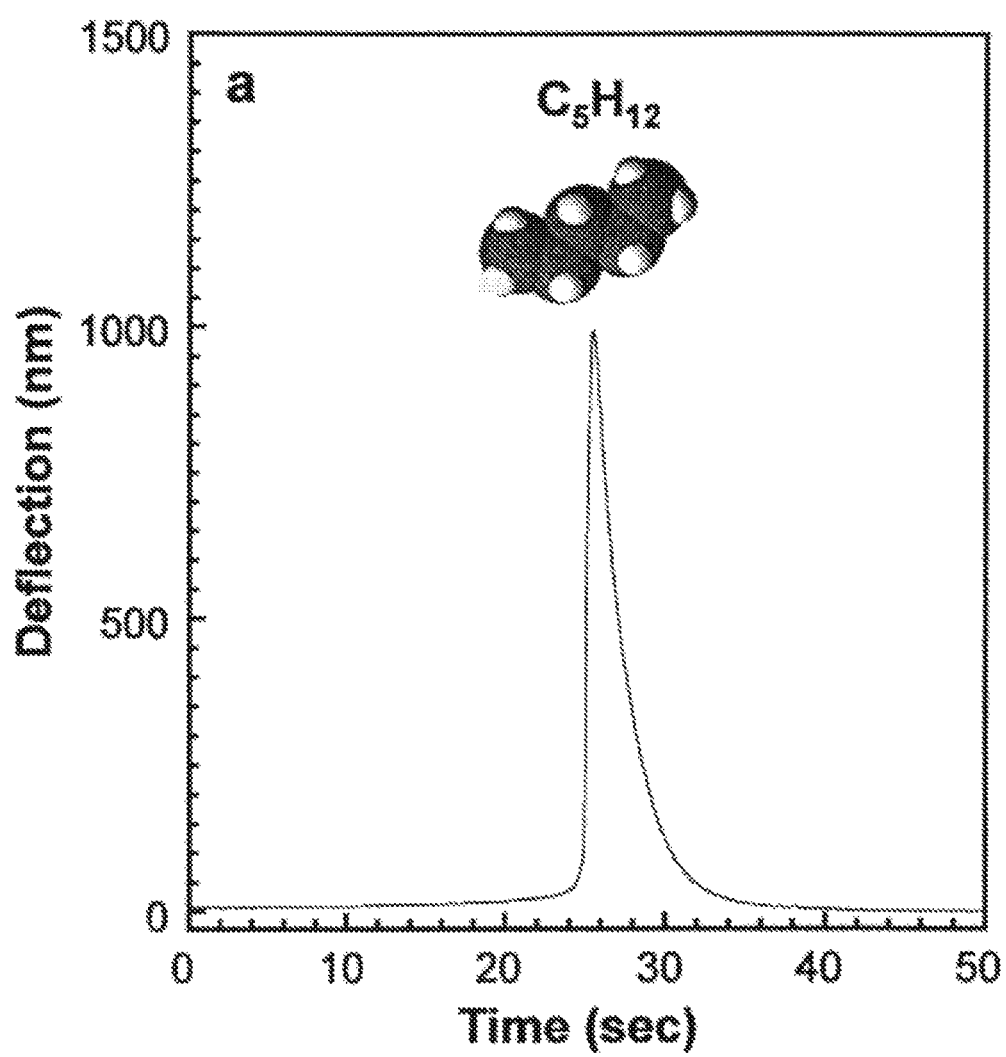
FIG. 10 is a drawing showing the deformation amount of the cantilever when a liquid sample (pentane) was vaporized and allowed to impinge on the cantilever.
Figure 11:
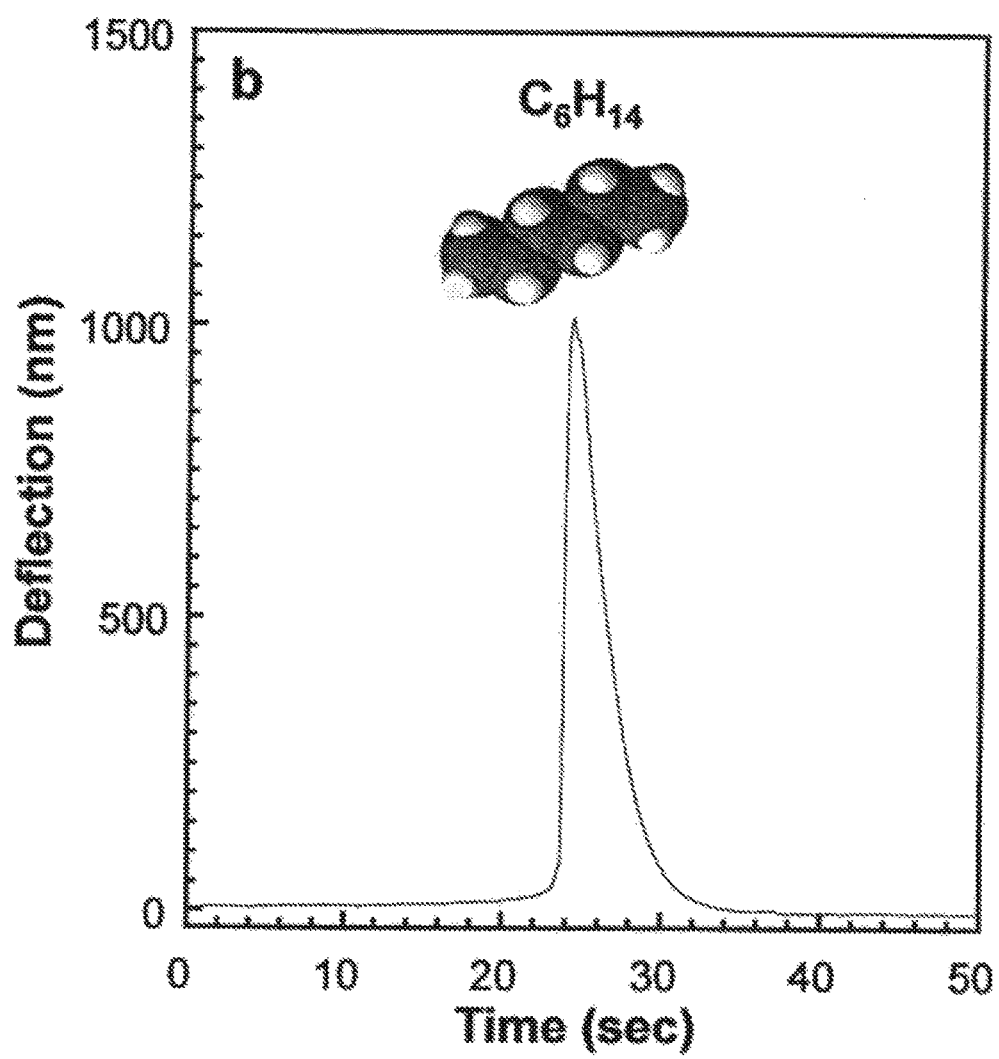
FIG. 11 is a drawing showing the deformation amount of the cantilever when a liquid sample (hexane) was vaporized and allowed to impinge on the cantilever.
Figure 12:
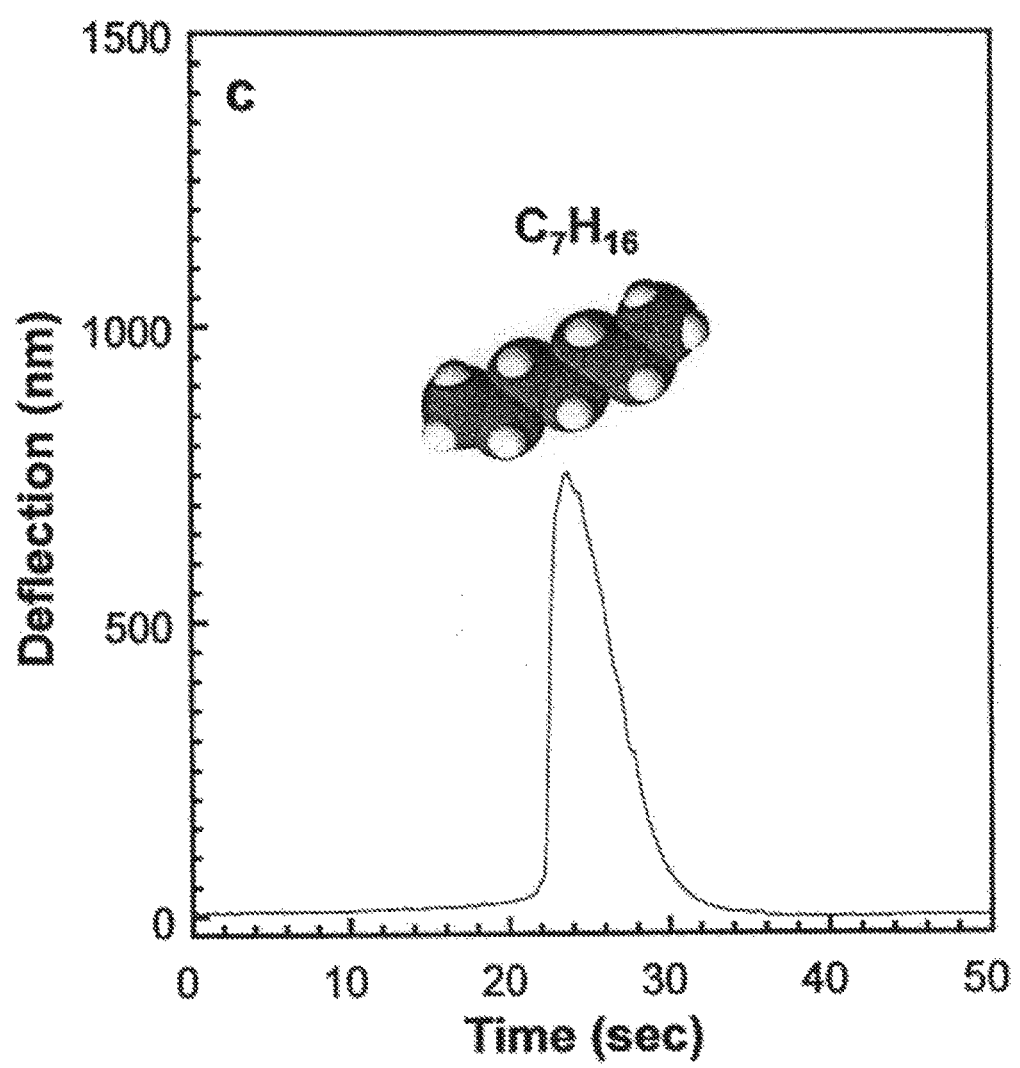
FIG. 12 is a drawing showing the deformation amount of the cantilever when a liquid sample (heptane) was vaporized and allowed to impinge on the cantilever.
Figure 13:
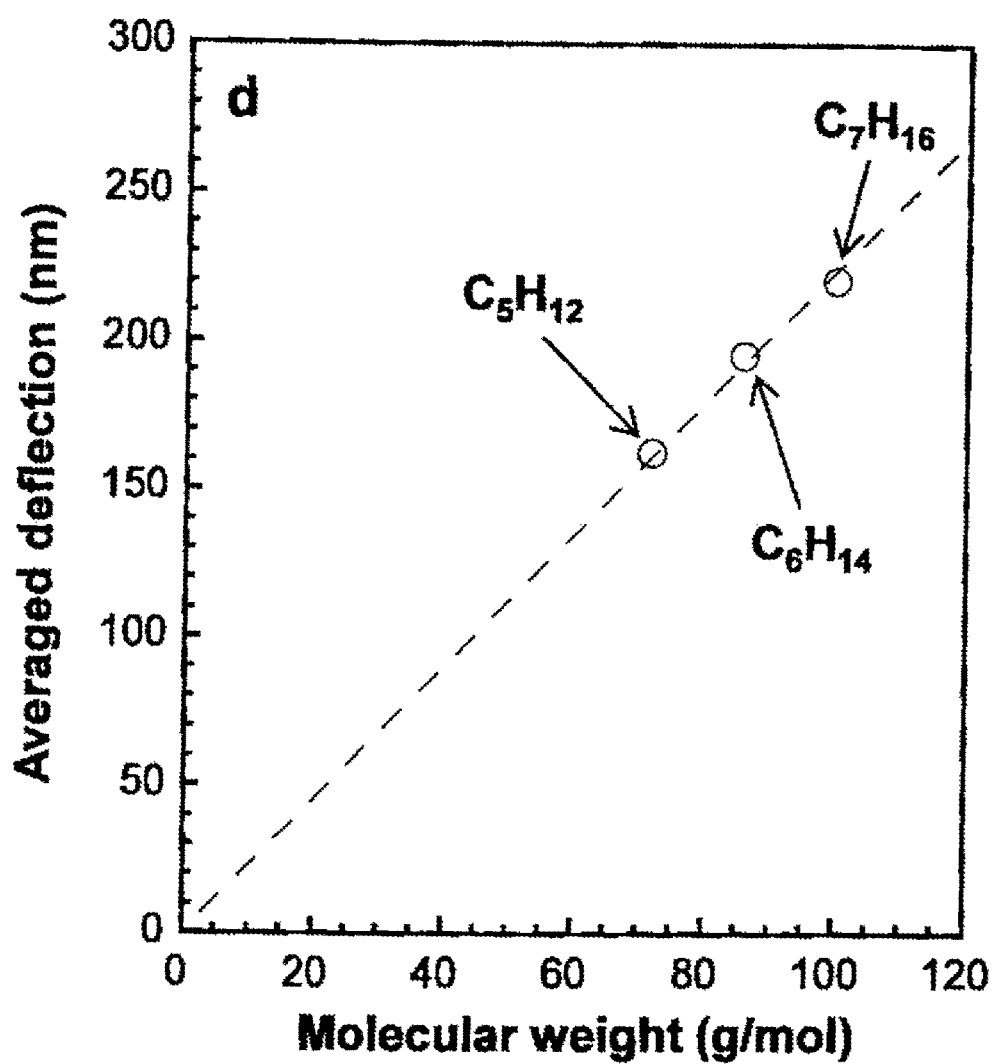
FIG. 13 is a drawing obtained by plotting the molecular weights of the corresponding liquid samples (pentane, hexane, heptane) with respect to area values obtained by integrating the respective peaks in FIGS. 10, 11 and 12.

The deformation amounts of the cantilever are shown in FIG. 10 (pentane), FIG. 11 (hexane) and FIG. 12 (heptane), and the measurement results of the flow rates of the vaporized samples are shown in FIG. 13.

As shown in FIGS. 10, 11 and 12, a single peak was observed in either of the cases, by the collision of the vaporized liquid sample (pentane, hexane, heptane) in the carrier gas with the cantilever. The areas obtained by integrating these peaks were 2598, 3120 and 3531, respectively, for pentane, hexane and heptane.

By plotting the area values obtained from FIGS. 10-12 against the molecular weights of pentane (7 s g/mol), hexane (86 g/mol) and heptane (100 g/mol), the linear relationship between the molecular weights and the area values was confirmed as shown in FIG. 13. This is similar to the case of the gas samples shown in FIG. 8.

<Example 4> Concentration of Gas Sample and Deformation Amount of Cantilever

As is also understood from Example 1, in the case when samples whose molecular weights are known are mixed, it becomes possible to calculate the concentration of each component from the deformation amount of the cantilever. As an example, an experiment for visualizing the diffusion property of the gas flowed from the nozzle in real-time was performed. In order to carry out this experiment, a pump that is driven by a piezoelectric element was connected to a chamber in which the above-mentioned cantilever is placed, whereby a device that can measure a concentration at an arbitrary point in the air was prepared. The nozzle diameter was 0.7 mm, and argon and helium were flowed at a flow rate of 150 mL/min. Setting the center point of the nozzle as an origin, and a tube connected to the pump was moved at 0.25 mm intervals in the horizontal direction and at 1 mm intervals in the vertical direction, and a gas sample was sucked at each point as a sample for a certain time. The deformation amount of the cantilever occurred at that time was measured by a digital holographic microscope, and the concentration of the gas was calculated.

Figure 14:
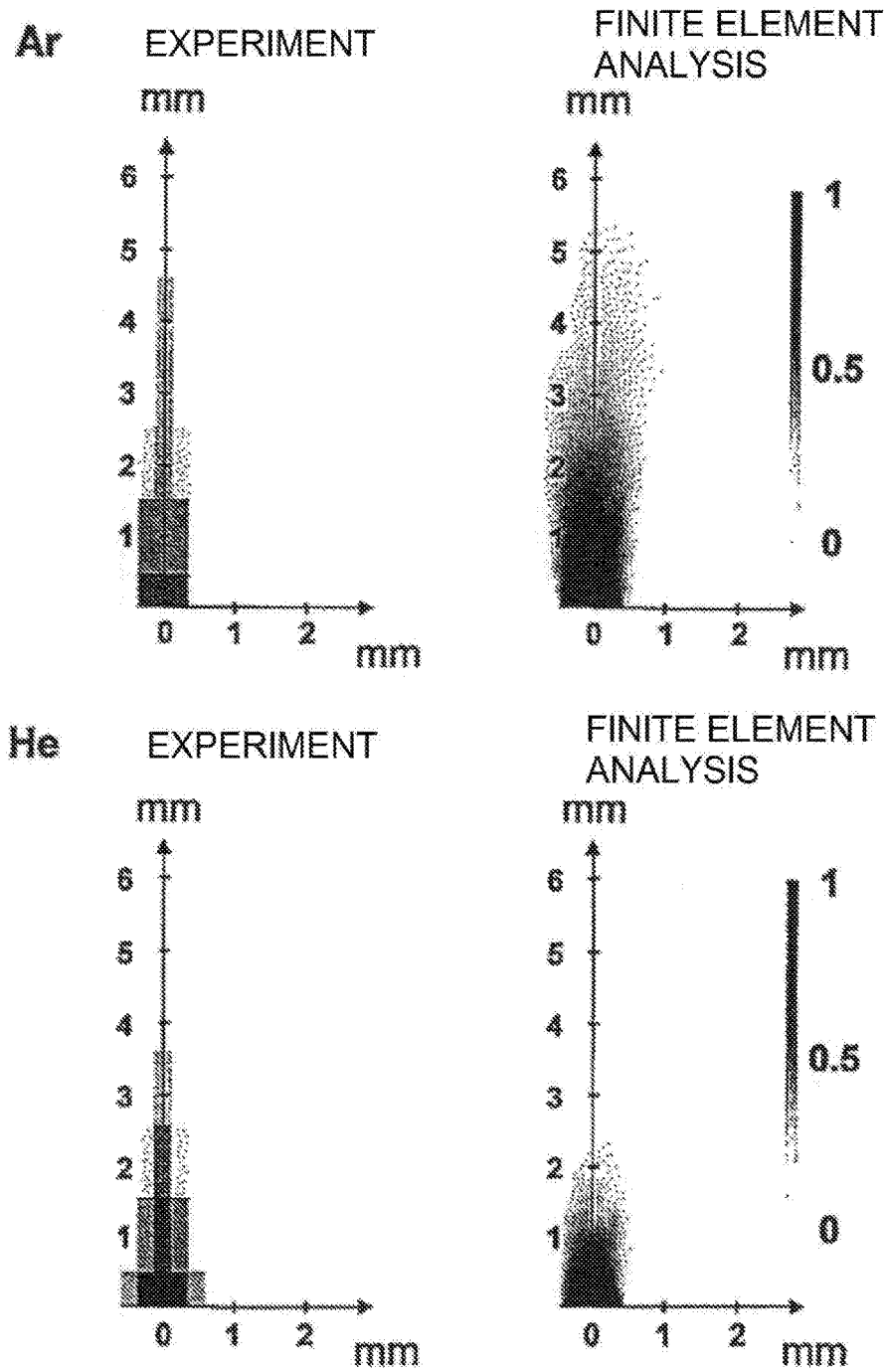
FIG. 14 is a drawing obtained by depicting the state of the diffusion of the gas sample (helium and argon) in the air by an experiment using the molecular weight measurement device of the present invention and a finite element analysis. An outlet of a nozzle is positioned at 0 mm on both the vertical axis and the horizontal axis, a gas sample is flowed in the vertical axis direction (upward), and the contrasting density in each graph shows the gas concentrations at the respective positions. Specifically, the nozzle diameter was 0.7 mm, and the flow rate of the gas was 150 mL/min. The center point of the nozzle was set as an origin, a tube connected with a pump was moved from the origin at 0.25 mm intervals in the horizontal direction and at 1 mm intervals in the vertical direction, and a sample of the gas was taken in every point for a certain time, and the deformation amount of the cantilever occurred during the sampling was measured by means of a digital holographic microscope, and the concentration of the gas was calculated.

As shown in FIG. 14, it was confirmed that argon and helium diffusing in the air can be experimentally visualized. These results are agreed well with the results of the finite element analysis. It is understood that the diffusion in the horizontal direction is large in the case of helium, whereas the diffusion in the vertical direction is large in the case of argon. This is explained by the fact that the diffusion coefficient of helium is about four times larger than that of argon.

Figure 15:
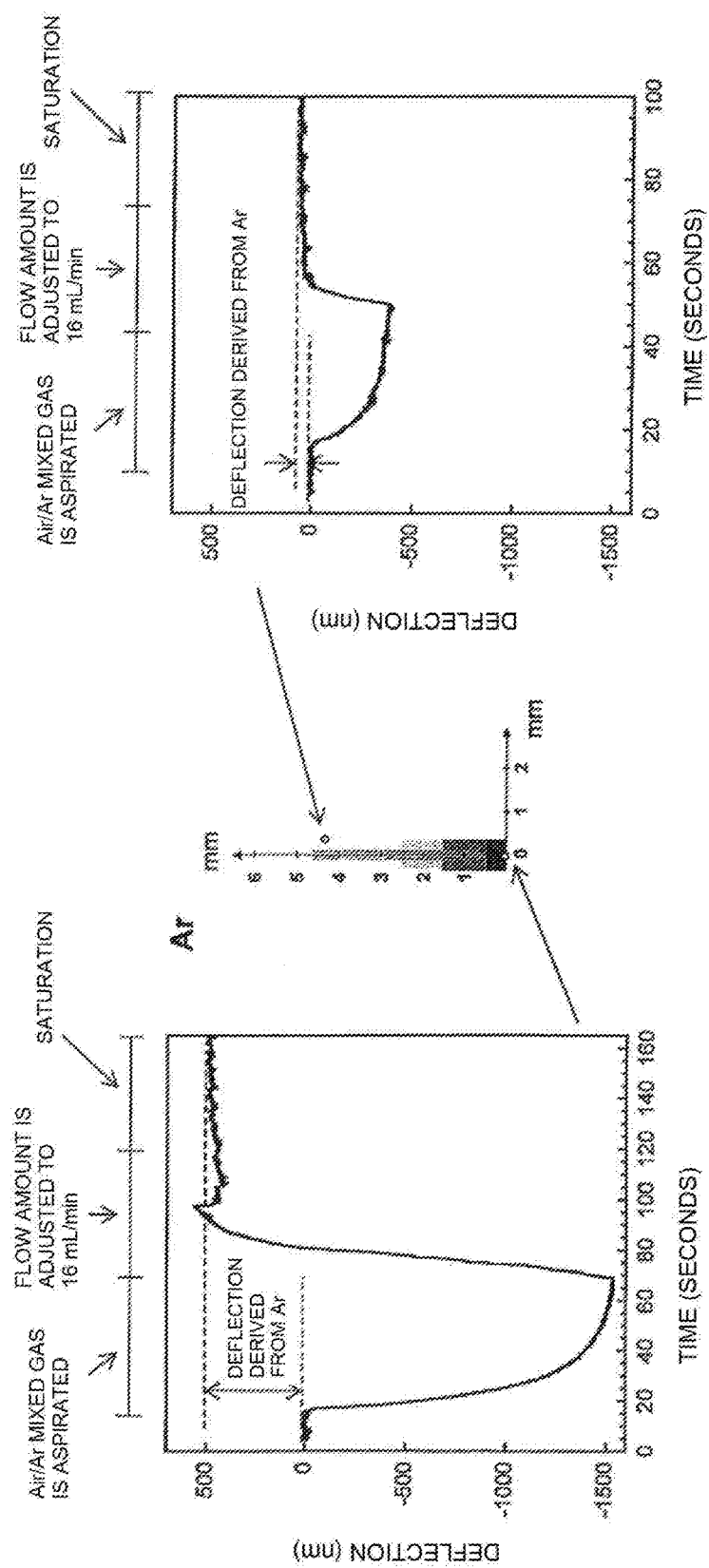
FIG. 15 is a drawing showing a means for determining a gas concentration at an arbitrary point in an real space by using the molecular weight measurement device of the present invention.

In this Example, the gas aspirated by the pump is a mixed gas of the gas sample flowed from the nozzle and air. Therefore, in order to visualize a concentration map as shown in FIG. 14, it is necessary to obtain a ratio of the gas sample to the air at each point. Here, the flow rate of the pump was kept constant (16 mL/min), and using the deformation amount of the cantilever which is generated when only air is aspirated as a reference, the increase or decrease from the reference was assumed to be due to the contribution of the gas sample. Specifically, as shown in FIG. 15 (left), it is understood that the deformation amount increases by about 500 nm at the center point of the nozzle as compared to the case of air only. On the other hand, as shown in FIG. 15 (right), the argon concentration is low at a place apart from the center point of the nozzle, and thus the difference of the deformation amount of the cantilever is small compared to that in the case of air only. By utilizing the relationship between the deformation amount of the cantilever at a flow rate of 16 mL/min and the molecular weight, which had been prepared in advance, the molecular weight of the mixed gas was calculated from the deformation amount of the cantilever obtained by this experiment. Thereafter, the gas sample concentration was determined with assuming that the obtained molecular weight was a weighted average of the gas sample and air.

As means for visualizing a gas concentration, methods utilizing infrared ray absorbability of molecules, and methods utilizing luminescence have been reported so far. However, either of the methods requires infrared ray absorbability or luminescence property of a molecule itself, and thus the species of the molecules that can be measured are limited. Therefore, it is difficult to use these means as standard means, and thus establishment of a more versatile means is desired. The molecular weight measurement method of the present invention can determine the molecular weight of a molecule without being affected by the properties of the molecule itself. Therefore, it is possible in principle to target all molecules, and applications in a quite broad scope are expected, for example, utilization in basic science such as evaluation of a diffusion coefficient of a gas, medical diagnosis technologies based on difference in diffusibility of exhaled breath and other biological gases and the like, and applications in quantitative observations of in-door environments, and the like.

<Example 5> Consideration of Drag Coefficient $C_D$ and Reynolds Number Re in Cantilever The value of the drag coefficient $C_D$ can be estimated as shown in the following Table 8 from the mathematical formula (9).

TABLE 8

| | He | $N_2$ | Air | Ar | $CO_2$ |
|---|---|---|---|---|---|
| $C_D$ | 29.75 | 1.565 | 1.519 | 1.075 | 0.9702 |

Furthermore, the drag coefficient $C_D$ can be generally determined based on an experiment or a simulation. In this Example, for the Reynolds number Re, the values that are calculated by using the mathematical formula (8) in the cases when the representative length l is the diameter of the pipe, and the width of the cantilever, respectively, are summarized in Tables 9 and 10.

TABLE 9

|    | He     | N$_2$ | Air   | Ar    | CO$_2$ |
|----|--------|-------|-------|-------|--------|
| Re | 0.8373 | 45.92 | 47.24 | 73.64 | 135.0  |

TABLE 10

|    | He     | N$_2$ | Air   | Ar    | CO$_2$ |
|----|--------|-------|-------|-------|--------|
| Re | 0.2512 | 13.78 | 14.17 | 22.09 | 40.49  |

Figure 16:
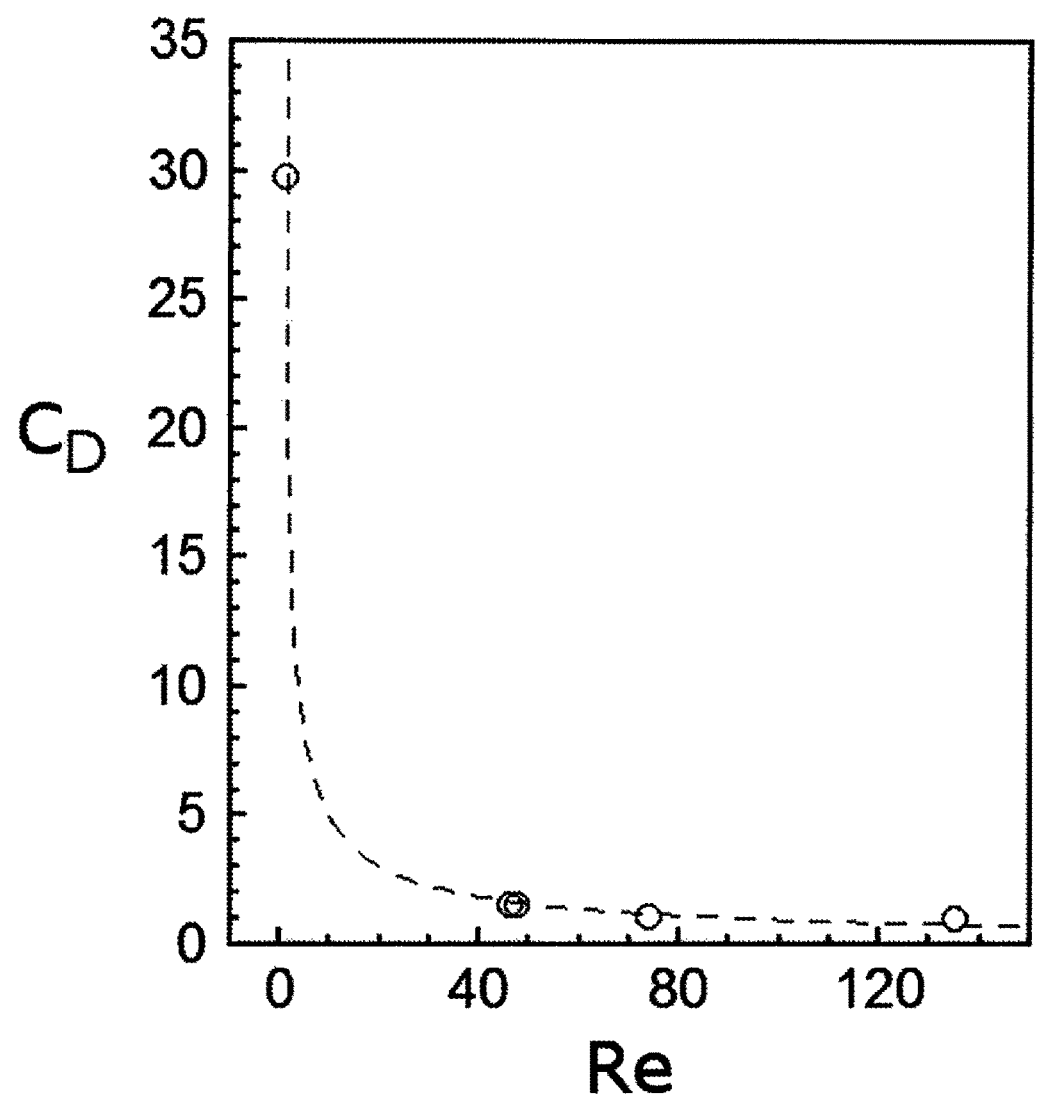
FIG. 16 is a drawing showing the relationship between drag coefficients ($C_D$) and Reynolds numbers (Re).

As indicated in Tables 8, 9 and 10, and FIG. 16, it is confirmed that the drag coefficient $C_D$ has a correlation with the Reynolds number Re.

As mentioned above, according to the method of the present invention, the molecular weight (M) of the gas sample, or of the gasified liquid sample or solid sample can be calculated based on the deformation amount of the structure (cantilever) by substituting the respective values into the parameters of the mathematical formula (3) or (17).

REFERENCE SIGNS LIST

1 Molecular weight measurement device
2 Gas feeding means
3 Flow rate controlling means
4 Chamber
5 Deformation measurement means
6 Flow rate controlling means
7 Calculation means
8 Cantilever

CITATION LIST

Patent Literature

Patent Literature 1: Japanese Patent Application Laid-Open No. 2013-015362

Non-Patent Literature

Non-patent Literature 1: J. Fritz, M. K. Baller, H. P. Lang, H. Rothuizen, P. Vettiger, E. Meyer, H. J. Guntherodt, C. Gerber, and J. K. Gimzewski, "Translating biomolecule recognition into nanomechanics," Science 288, 316-318 (2000).
Non-patent Literature 2: M. K. Baller, H. P. Lang, J. Fritz, C. Gerber, J. K. Gimzewski, U. Drechsler, H. Rothuizen, M. Despont, P. Vettiger, F. M. Battiston, J. P. Ramseyer, P. Fornaro, E. Meyer, and H. J. Guntherodt, "A cantilever array-based artificial nose," Ultramicroscopy 82, 1-9 (2000).
Non-patent Literature 3: Faith A. Morrison, "Data Correlation for Drag Coefficient for Sphere," Department of Chemical Engineering, Michigan Technological University, Houghton, Mich.

The invention claimed is:

1. A method of measuring a molecular weight, comprising the steps of:
    providing a structure that exhibits a change in characteristic when a sample in a gas state impinges a surface thereof, wherein the sample in a gas state is at least one selected from the group consisting of a gaseous sample, a gasified liquid sample, and a gasified solid sample, and wherein the change in characteristic is at least one selected from the group consisting of a mechanical deformation, an optical change, an electric change, and a magnetic change;
    causing the change in characteristic of the structure by letting the sample in a gas state impinge on the structure; and
    obtaining a molecular weight of the sample in a gas state based on the amount of the change.

2. The method of measuring a molecular weight according to claim 1, wherein the change in characteristic is a mechanical deformation, and the method comprises the steps of deforming the structure by letting the sample in a gas state impinge on the structure, and obtaining the molecular weight of the gas based on the amount of the deformation of the structure.

3. The method of measuring a molecular weight according to claim 2,
    wherein a drag force $F_D$ by the sample in a gas state is calculated based on the amount of the deformation of the structure; and
    the molecular weight M of the gas is obtained based on the following approximation mathematical formula:

[Mathematical Formula 1]

$$F_D = \frac{PV^2 C_D A}{2RT} M$$

wherein, in the approximation mathematical formula, R is a gas constant, T is a temperature of the gas, P is a pressure of the gas, V is a relative velocity of the gas, $C_D$ is a drag coefficient, and A is a surface area on which the drag force is applied.

4. The method of measuring a molecular weight according to claim 1, wherein the sample in a gas state is provided as a jet flow to the structure.

5. The method of measuring a molecular weight according to claim 4,
    wherein the jet flow is an axially symmetric jet flow,
    wherein the change in characteristic is a mechanical deformation,
    wherein the method comprises the steps of deforming the structure by letting the sample in a gas state impinge on the structure, and obtaining the molecular weight of the gas based on the amount of the deformation of the structure,
    wherein a drag force $F_D$ by the sample in a gas state is calculated based on the amount of the deformation of the structure, and
    wherein the drag force is provided by the following approximation mathematical formula:

[Mathematical Formula 2]

$$F_D = \frac{9w C_D L M^3 P^3 Q^4}{8\pi^4 \mu^2 l^4 H^2 R^3 \left( \frac{3x^2 M^2 P^2 Q^2}{16\pi^2 \mu^2 l^2 H^2 R^2 T^2} + 1 \right)^4 T^3}$$

wherein, in the approximation mathematical formula, μ is a kinetic viscosity coefficient of a gas that flows out at a flow rate Q from an outlet of a pipe having a diameter of l as the axially symmetric jet flow and impinge at a drag coefficient $C_D$ on the structure; the structure is an object having a width w and a length L located at a distance H from the outlet; x is a distance in the vertical direction with respect to a jet flow axis from a center point of the outlet; M is the molecular weight of the gas; P is a pressure of the gas; R is a gas constant and T is a temperature of the gas.

6. The method of measuring a molecular weight according to claim 5, wherein the structure is a cantilever.

7. The method of measuring a molecular weight according to claim 6, wherein the amount of the deformation z (x) of the cantilever is provided by the following approximation mathematical formula:

[Mathematical Formula 6]

$$z(x) = \left[ -16\pi^2 \alpha \mu^2 l^2 wxH^2 \{\mathrm{atan}(\beta L) - \mathrm{atan}(\beta x)\} R^2 T^2 - 4\sqrt{3}\pi\alpha\mu l wxH(x-L)MPQRT - 3\alpha w\{(3x-2L)L^2 \mathrm{atan}(\beta L) - x^3 \mathrm{atan}(\beta x)\} M^2 P^2 Q^2 \right] / \left[ 2^{9/2} \pi^2 l^{5/2} E\sqrt{H} \, IMPRT \right]$$

wherein $$\beta = \frac{\sqrt{3}\,MPQ}{4\pi\mu lHRT}, \quad I = \frac{wt^3}{12},$$

wherein t is a thickness of the cantilever,

E is a Young's Modulus of the cantilever,

α is a number obtained from a relationship between a Reynolds number Re and the drag coefficient $C_D$ obtained by the following approximation mathematical formula:

[Mathematical Formula 3]

$$C_D = \frac{\alpha}{\sqrt{Re}},$$

and a free end of the cantilever is placed on the jet flow axis with x=0.

8. The method of measuring a molecular weight according to claim 7, wherein the Reynolds number Re is provided by the following formula:

[Mathematical Formula 4]

$$Re = \frac{\rho Vl}{\mu},$$

wherein p is a density of the gas, and V is a relative velocity of the gas.

9. The method of measuring a molecular weight according to claim 7, wherein the Reynolds number Re is provided by the following formula:

[Mathematical Formula 5]

$$Re = \frac{\rho Vw}{\mu},$$

wherein p is a density of the gas, and V is a relative velocity of the gas.

10. The method of measuring a molecular weight according to claim 1, wherein the structure is a cantilever.

11. The method of measuring a molecular weight according to claim 1, wherein the structure is deformed by moving the structure in a space containing the sample in a gas state.

12. The method of measuring a molecular weight according to claim 1, wherein the change in characteristic is a mechanical deformation and the amount of the deformation of the structure is measured by a deformation measurement means that is capable of optically detecting deformation of the structure.

13. A molecular weight measurement apparatus comprising:

a chamber having an inlet from which a sample in a gas state is introduced, and having a cantilever therein, wherein the sample in a gas state is at least one selected from the group consisting of a gaseous sample, a gasified liquid sample, and a gasified solid sample;

a sample feeding means feeding the sample in a gas state from the inlet into the chamber to let the sample in a gas state impinge on the cantilever;

a deformation amount measurement means measuring an amount of deformation of the cantilever associated with impingement of the sample in a gas state; and a calculation means calculating a molecular weight of the sample in a gas state based on the amount of the deformation of the cantilever.

14. The molecular weight measurement apparatus according to claim 13, wherein the cantilever has a width w and a length L, and is disposed at a distance H from the outlet of a pipe having a diameter l, and the calculation means is arranged to be capable of calculating a molecular weight M of a gas based on a relational formula between a deformation amount z (x) of the cantilever and the molecular weight M of the gas, provided by the following approximation mathematical formula:

[Mathematical Formula 7]

$$z(x) = \left[ -16\pi^2 \alpha \mu^2 l^2 wxH^2 \{\mathrm{atan}(\beta L) - \mathrm{atan}(\beta x)\} R^2 T^2 - 4\sqrt{3}\pi\alpha\mu l wxH(x-L)MPQRT - 3\alpha w\{(3x-2L)L^2 \mathrm{atan}(\beta L) - x^3 \mathrm{atan}(\beta x)\} M^2 P^2 Q^2 \right] / \left[ 2^{9/2} \pi^2 l^{5/2} E\sqrt{H} \, IMPRT \right]$$

wherein $$\beta = \frac{\sqrt{3}\,MPQ}{4\pi\mu lHRT}, \quad I = \frac{wt^3}{12},$$

wherein t is a thickness of the cantilever,

μ is a kinetic viscosity coefficient of a gas that is flowed out at a flow rate Q from an outlet of a pipe having a diameter of l as an axially symmetric jet flow and impinges on the structure with a drag coefficient $C_D$; x is a distance in the vertical direction with respect to the jet flow axis from a center point of the outlet; E is a Young's Modulus of the cantilever; P is a pressure of the gas; R is a gas constant T is a temperature of the gas; and α is a number obtained from a relationship between a Reynolds number Re and the drag coefficient $C_D$ represented by the following approximation mathematical formula:

[Mathematical Formula 8]
$$C_D = \frac{\alpha}{\sqrt{Re}},$$

and
wherein a free end of the cantilever is located at the position on the jet flow axis with x=0.

15. The molecular weight measurement apparatus according to claim 14, wherein the Reynolds number Re is provided by the following formula:

[Mathematical Formula 9]
$$Re = \frac{\rho V l}{\mu},$$

wherein p is a density of the gas, and V is a relative velocity of the gas.

16. The molecular weight measurement apparatus according to claim 14, wherein the Reynolds number Re is provided by the following formula:

[Mathematical Formula 10]
$$Re = \frac{\rho V w}{\mu},$$

wherein p is a density of the gas, and V is a relative velocity of the gas.

* * * * *